(12) United States Patent
Harashima et al.

(10) Patent No.: US 7,456,020 B2
(45) Date of Patent: Nov. 25, 2008

(54) METHOD FOR MODIFYING CHROMOSOMES

(75) Inventors: Satoshi Harashima, Osaka (JP);
Yoshinobu Kaneko, Osaka (JP);
Minetaka Sugiyama, Osaka (JP)

(73) Assignee: Osaka University (JP)

( * ) Notice: Subject to any disclaimer, the term of this patent is extended or adjusted under 35 U.S.C. 154(b) by 728 days.

(21) Appl. No.: 10/659,326

(22) Filed: Sep. 11, 2003

(65) Prior Publication Data
US 2004/0224415 A1 Nov. 11, 2004

(30) Foreign Application Priority Data
Nov. 22, 2002 (JP) .............................. 2002-339259

(51) Int. Cl.
*C12N 15/00* (2006.01)
*C12N 15/74* (2006.01)
*C12P 19/34* (2006.01)

(52) U.S. Cl. .................... 435/440; 435/320.1; 435/471; 435/473; 435/476; 435/483; 435/91.2

(58) Field of Classification Search ....................... None
See application file for complete search history.

(56) References Cited

FOREIGN PATENT DOCUMENTS

WO WO 98/54348 12/1998

OTHER PUBLICATIONS

Kim et al. A versatile and general splitting technology for generating targeted YAC subclones. Appl Microbiol Biotechnol. 69(1):65-70. 2005.*
Heus, Joris J. et al., "Centromeric and Noncentromeric ADE2-Selectable Fragmentation Vectors for Yeast Artificial Chromosomes in AB1380," Genome Research 7: 657-660 (1997).
European Search Report, May 16, 2004.
Ascenzioni, et al., "Functional Telomere Formation in Yeast Using Synthetic $C_4A_2$ Sequences," *Plasmid* 23, pp. 16-26 (1990).
Reeves, et al., "Yeast Artificial Chromosome Modification and Manipulation," *Methods in Enzymology*, vol. 216, Methods Enzymol. 1992;216:584-603.
Pavan, et al, "High-efficiency Yeast Artificial Chromosome Fragmentation Vectors," *Gene*, 106 (1991) pp. 125-127.
Pluta, et al., "Recombination Occurs During Telomere Formation in Yeast," *Nature*, vol. 337, Feb. 2, 1989.

Vollrath, et al., "Physical Mapping of Large DNA by Chromosome Fragmentation," *Proc. Natl. Acad. Sci. USA*, vol. 85, pp. 6027-6031, Aug. 1988.
Widianto, et al., "Creating a *Saccharomyces cerevisiae* Haploid Strain Having 21 Chromosomes," *Journal of Bioscience and Bioengineering*, vol. 95, No. 1, pp. 89-94, 2003.
Widianto, et al., "One-Step Splitting of a Chromosome in Haploid Cells of *Saccharomyces cerevisiae* and Its Effect on the Cell Proliferation," *Journal of Fermentation and Bioengineering*, vol. 82, No. 3, pp. 199-204, 1996.
Shampay, et al., "DNA Sequences of Telomeres Maintained in Yeast," *Letters to Nature*, vol. 310, Jul. 12, 1984, pp. 154-157.
Murray, et al., "Characterization of Two Telomeric DNA Processing Reactions in *Saccharomyces cerevisiae*," *Molecular and Cellular Biology*, Nov. 1988, pp. 4642-4650.
Widianto, et al., "One-Step Splitting of a Chromosome in Haploid Cells of *Saccharomyces cervisiae* and Its Effect on the Cell Proliferation," *Journal of Fermentation and Bioengineering*, vol. 82, No. 3, pp. 199-204, 1996.
Kitada, et al., "Cloning of the *Candida glabrata* TRP1 and HIS3 Genes, and Construction of their Disruptant Strains by Sequential Integrative Transformation," *Gene*, 165, (1995), pp. 203-206.
Güldener, et al., "A New Efficient Gene Disruption Cassette for Repeated Use in Budding Yeast," *Nucleic Acids Research*, 1996, vol. 24, No. 13, pp. 2519-2524.
Winston, et al., "Construction of a Set of Convenient *Saccharomyces cervisiae* Strains that are Isogenic to S288C," *Yeast*, vol. 11: pp. 53-55 (1995).

\* cited by examiner

*Primary Examiner*—Sumesh Kaushal

(57) ABSTRACT

The present invention provides a simple method for splitting and loss of a chromosome in yeast. The method for modifying a chromosome in yeast includes preparing a linear chromosome splitting vector (1) having a target sequence (a), a marker gene sequence and $(C_4A_2)_n$ sequence in this order; preparing a linear chromosome splitting vector (2) having a target sequence (b), a centromere sequence of a yeast chromosome and $(C_4A_2)_n$ sequence in this order; and introducing the chromosome splitting vectors (1) and (2) into yeast. Herein, n is each independently an integer of 6 to 10. Although this chromosome splitting vector has a repetitive sequence of 5'-CCCCAA-3', it can be amplified specifically with PCR, so that a chromosome splitting vector can be prepared significantly simply and easily, compared with the conventional DNA splitting method. It seems that a yeast telomere sequence is bound to the $(C_4A_2)_n$ sequence of the split chromosome generated by splitting with the chromosome splitting vector, and therefore the fragment can function as an intact chromosome.

2 Claims, 16 Drawing Sheets

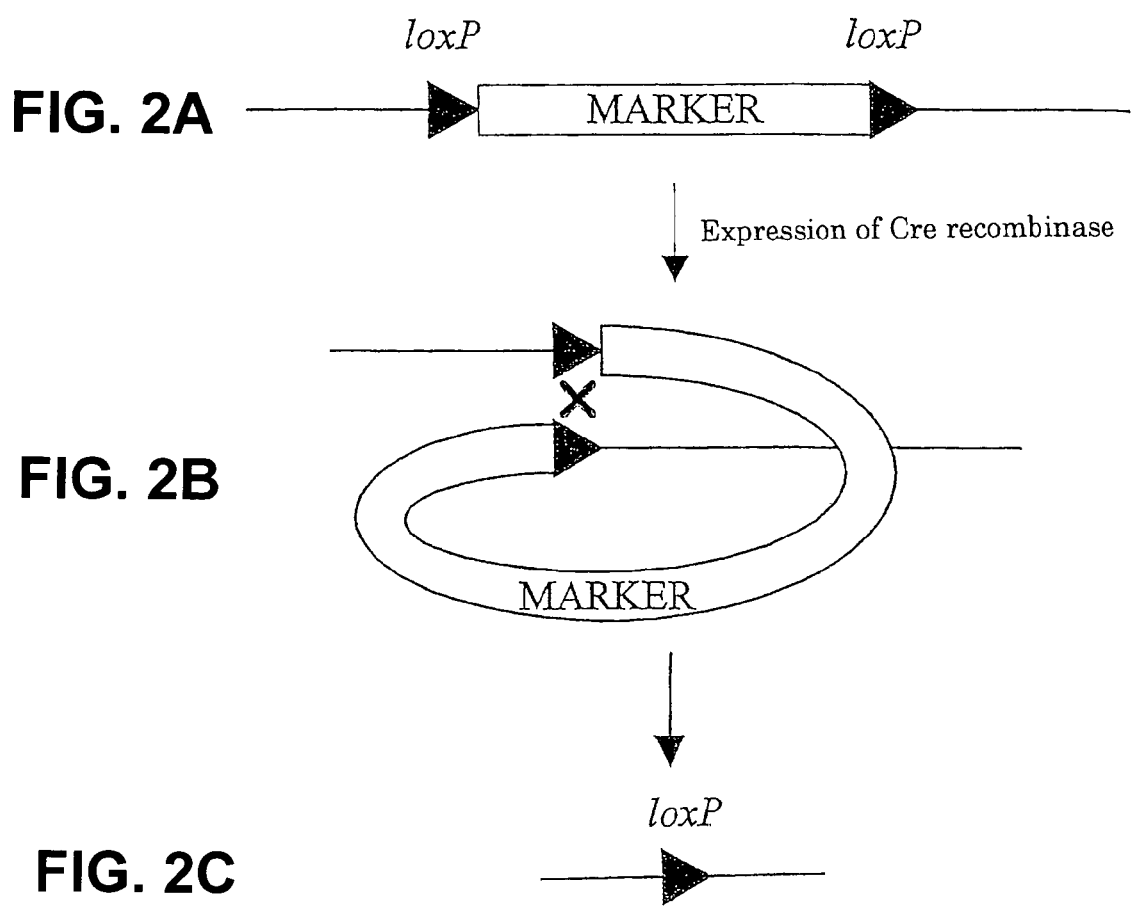

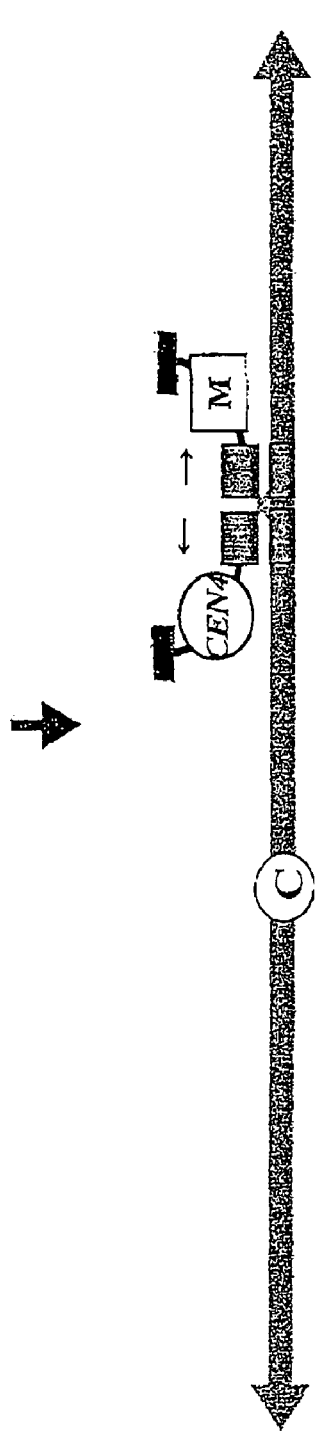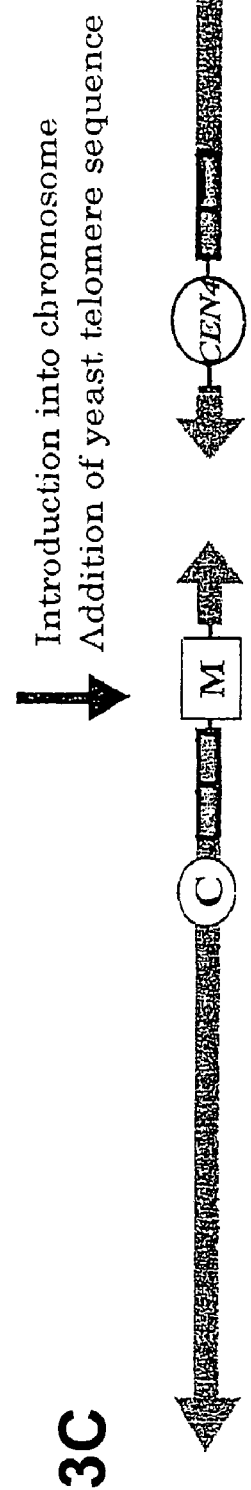
FIG. 3A
FIG. 3B
FIG. 3C

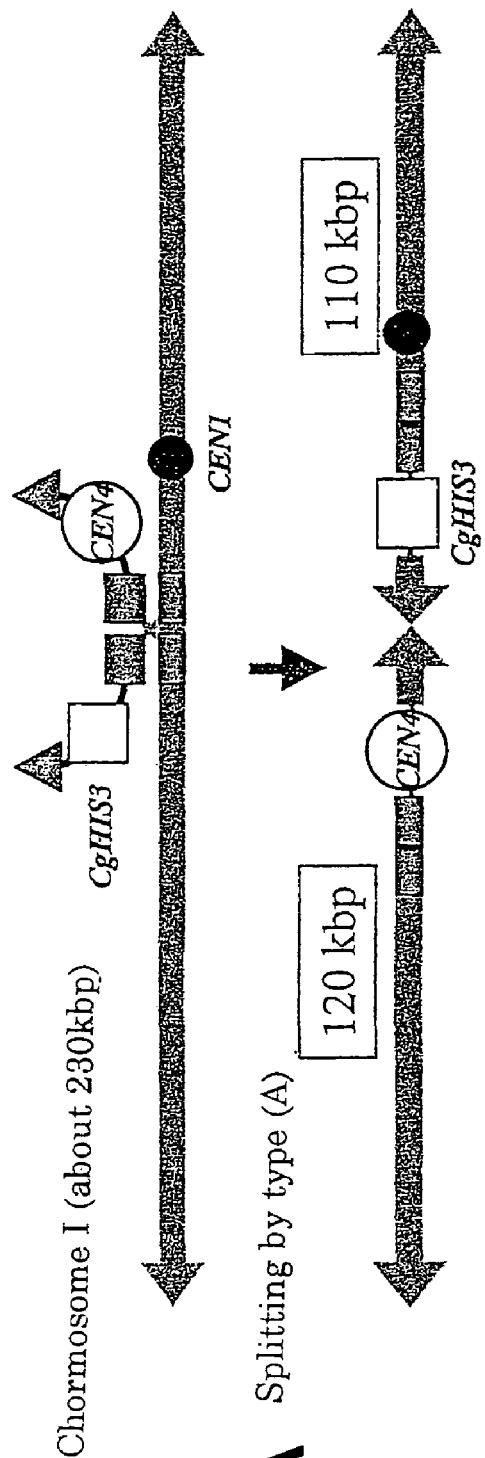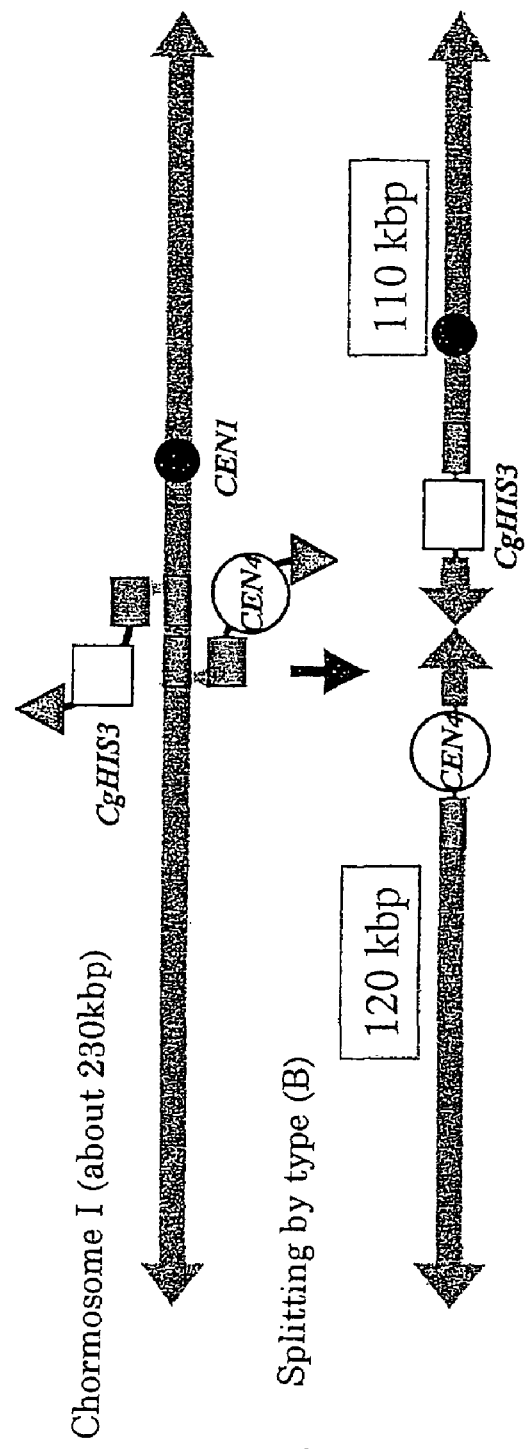
FIG. 6A  Splitting by type (A)
FIG. 6B  Splitting by type (B)

PCR product 7: 1.8kbp

PCR product 8: 2.1kbp 1,6: Molecular weight marker
2,3: PCR product 7
4,5: PCR product 8

2.1 kbp
1.8 kbp

SEQUENCE LISTING

```
<160> NUMBER OF SEQ ID NOS: 20

<210> SEQ ID NO 1
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 1
ctctctagat aacaccgatc agatgcaca                                      29

<210> SEQ ID NO 2
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 2
ctcctcgaga aacttgctct gctaactca                                      29

<210> SEQ ID NO 3
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 3
ctcgaattcg gccattctca tgaagaata                                      29

<210> SEQ ID NO 4
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 4
ctcgaattct ctaagaggtg atacttatt                                      29

<210> SEQ ID NO 5
<211> LENGTH: 99
<212> TYPE: DNA
<213> ORGANISM: Artificial Sequence
<220> FEATURE:
```

```
<223> OTHER INFORMATION: Other Information: Artificial sequence is a
      primer.

<400> SEQUENCE: 5
gaatgctatg ttgtggttag cgacctgccc cttgccaaat ctatatcacc acttccttag      60
catgtaatca tttacttaaa ggaaacagct atgaccatg                            99

<210> SEQ ID NO 6
<211> LENGTH: 56
<212> TYPE: DNA
<213> ORGANISM: Artificial Sequence
<220> FEATURE:
<223> OTHER INFORMATION: Other Information: Artificial sequence is a
      primer.

<400> SEQUENCE: 6
ccccaacccc aacccccaacc ccaaccccaa ccccaatcga ggtcgacggt atcgat         56

<210> SEQ ID NO 7
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 7
gttgaaaagg aaatcaacgt tacaaagtgc agttttttgt attattttcc tattatcctc      60
ttcttttcct ttgtttcagg ggaaacagct atgaccatg                            99

<210> SEQ ID NO 8
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 8
tttaagtaaa tgattacatg ctaaggaagt ggtgaataag atttggcaag gggcaggtcg      60
ctaaccacaa catagcattc ggaaacagct atgaccatg                            99

<210> SEQ ID NO 9
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 9
cctgaaacaa aggaaaagaa gaggataata ggaaaataat acaaaaaact gcactttgta      60
acgttgattt cctttccaac ggaaacagct atgaccatg                            99

<210> SEQ ID NO 10
<211> LENGTH: 60
<212> TYPE: DNA
<213> ORGANISM: Artificial Sequence
<220> FEATURE:
<223> OTHER INFORMATION: Other Information: Artificial sequence is a
      primer.

<400> SEQUENCE: 10
caagaaatat cttgaccgca gtgaactgtg ggaatactca ggtatacagc tatgaccatg      60
```

```
<210> SEQ ID NO 11
<211> LENGTH: 60
<212> TYPE: DNA
<213> ORGANISM: Artificial Sequence
<220> FEATURE:
<223> OTHER INFORMATION: Other Information: Artificial sequence is a
      primer.

<400> SEQUENCE: 11
gaaaaaataa tggttgctaa gagattcgaa ctcttgcatc ttacgacagc tatgaccatg      60

<210> SEQ ID NO 12
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 12
ctcgtcgacg gccattctca tgaagaata                                         29

<210> SEQ ID NO 13
<211> LENGTH: 29
<212> TYPE: DNA
<213> ORGANISM: Artificial Sequence
<220> FEATURE:
<223> OTHER INFORMATION: Other Information: Artificial sequence is a
      primer.

<400> SEQUENCE: 13
ctcctcgagt ctaagaggtg atacttatt                                         29

<210> SEQ ID NO 14
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 14
ggtcttcatc ctccatttgg tcaatgcggc caacaatacg gatttcctcc tcattggagc      60
gcagagaccc taacaacaca cttcgtacgc tgcaggtcg                              99

<210> SEQ ID NO 15
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 15
tgtgtggtca tgttcagcgt gagcaaaatc agtcggaaag tgaacgagaa ttggaatgtg      60
gaagacggac atatcactga cttcgtacgc tgcaggtcg                              99

<210> SEQ ID NO 16
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 16
```

```
ttataatgag caagtcgata caaggactgc ccataaagtg ggaggagtac gccgctgatg    60
aagtggtttt gctggtacct cttcgtacgc tgcaggtcg                          99

<210> SEQ ID NO 17
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 17
tatatgattt tgtgttcgtt tttcgtcttg cgaaaggcat ccccaatggc ttgtttcatt    60
gatccatcag tgtggctcgt cttcgtacgc tgcaggtcg                          99

<210> SEQ ID NO 18
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 18
gaccagtgaa gaggaattga ataagtagaa cttgggcaat acttataacg gcaatgataa    60
tgataatcaa tatagataac cttcgtacgc tgcaggtcg                          99

<210> SEQ ID NO 19
<211> LENGTH: 99
<212> TYPE: DNA
<213> ORGANISM: Artificial Sequence
<220> FEATURE:
<223> OTHER INFORMATION: Other Information: Artificial sequence is a
      primer.

<400> SEQUENCE: 19
acgaagactt tgaactattt gagagccaga gaatggagaa acatgtctac cgtcaattcc    60
accgaatcaa ggttgacttg cttcgtacgc tgcaggtcg                          99

<210> SEQ ID NO 20
<211> LENGTH: 56
<212> TYPE: DNA
<213> ORGANISM: Artificial Sequence
<220> FEATURE:
<223> OTHER INFORMATION: Other Information: Artificial sequence is a
      primer.

<400> SEQUENCE: 20
ccccaacccc aaccccaacc ccaaccccaa ccccaaaggc cactagtgga tctgat        56
```

METHOD FOR MODIFYING CHROMOSOMES

CROSS-REFERENCE TO RELATED APPLICATIONS

This application claims the priority of Japanese Patent Application No. 2002-339259, entitled "Method for Modifying Chromosomes," filed on Nov. 22, 2002. The entire contents and disclosure of which are hereby incorporated by reference.

BACKGROUND OF THE INVENTION

1. Field of the Invention

The present invention relates to a method for modifying a chromosome of yeast, employing yeast chromosome splitting vectors. More specifically, the present invention relates to a method for modifying a chromosome, employing two linear chromosome splitting vectors.

2. Description of the Related Art

The development of recombinant DNA technology has led to the development of techniques for modifying or manipulating genes as desired, and has made it possible to introduce modified genes into various organisms.

Techniques for modifying DNA include site-specific mutagenesis, treatments with restriction enzymes, and PCR. However, these techniques are only applicable to genes having a limited size such as about 10 kbp, at most about 40 kbp. Development of techniques for modifying large size DNA such as a chromosome has just begun.

Yeast is a useful organism that has been used in the fermentation industry for a long time. The chromosome of yeast can be modified by chromosome modification techniques such as splitting or loss of a chromosome so as to obtain information about, for example, the necessary number, length, and an amount of chromosomes. Based on such information, principle of yeast genome function and organization is expected to be constructed. If this principle is constructed, it may be possible that a desired substance can be produced efficiently by yeast in which unnecessary genes, for example, energy consuming genes are removed. Furthermore, if a desired region of a chromosome can be transferred into another yeast, the chromosome function of yeast can be analyzed so as to breed useful yeast.

DNA libraries including a large size DNA (e.g., 200 kbp or more) of plant chromosomes have been prepared by using, for example, a yeast artificial chromosome vector (YAC vector). If this large size DNA can be separated or manipulated as desired in accordance with various purposes, it may be possible to accelerate a development of plant biotechnology including breeding of useful transgenic plants that have not existed before. Further, it may also be possible to accelerate a development of basic biology for animals and plants, for example, elucidation of structure and function of animal and plant chromosomes, speed-up of positional cloning, simple and easy assay for animal and plant gene function, and construction of artificial chromosomes for animals or plants.

In this context, it has been attempted to manipulate chromosomes, for example, to split or loss of chromosomes of yeast or animal or plant. In order to stabilize a chromosome in yeast, it is necessary that a telomere sequence is present at a terminal of the chromosome. For this reason, the conventional technique for splitting a chromosome in yeast utilizes a phenomenon that the telomere sequence of the yeast is added to the telomere sequence derived from Tetrahymena rDNA (hereinafter referred to as "Tr sequence") at a high frequency in order to stabilize the split chromosome (see Shampay et al. (1984) Nature (London) 310, 154-157). FIGS. 15A to 15D show the outline of this conventional technique for splitting a chromosome. This technique is based on the following phenomenon: when a vector haboring centromere (C), telomere repetitive sequence (Tr-Tr) derived from Tetrahymena rDNA that are placed in opposite directions to each other, a selection marker (M) for a yeast transformation, and any target sequence is introduced into a yeast chromosome by transformation (FIG. 15A), homologous recombination occurs within the target sequence (FIG. 15B). Then, telomere resolution occurs at the Tr-Tr sequence that has been introduced into the chromosome so as to split the chromosome (FIG. 15C), followed by addition of telomere sequence of the yeast to the dissociated terminal (Tr sequence) of the split chromosomes (FIG. 15D).

FIGS. 16A and 16B show the Tr sequence derived from Tetrahymena. The Tr sequence consists of about 700 bp, in which an AT rich portion of about 400 bp is followed by a repetitive sequence element of 5'-CCCCAA-3' ($C_4A_2$) of about 300 bp. It seems that this repetitive sequence serves as a signal to which the telomere sequence of the yeast can be added effectively (FIG. 16A). It has been reported that the telomere sequence of the yeast can be added to a terminal sequence $(C_4A_2)_6$ consisting of only 6 repeats of $C_4A_2$ (FIG. 16B) (see Murray et al., (1988) Mol. Cell. Biol. 8(11), 4642-4650).

There has been a report of an attempt to split a yeast chromosome utilizing the phenomenon shown in FIG. 16A, for example, using a yeast chromosome vector pCSV1 having a centromere gene (CEN4) of the yeast, a marker gene (URA3), two telomere sequences that are placed in opposite directions each other and a HIS3 gene as stuffer DNA between the two telomere sequences (see Japanese Laid-Open Patent Publication No. 10-84945).

FIG. 17 shows the splitting of a yeast chromosome with this splitting vector pCSV1. In FIG. 17, the pCSV1 has CEN4, URA3 (not shown), Tr sequences that are placed in opposite directions each other, and a stuffer DNA (X) between the two Tr sequences. The splitting includes the steps of: (Step 1) introducing a target sequence (Y) into the splitting vector pCSV1, wherein the target sequence (Y) has a splitting site; (Step 2) removing the stuffer DNA (X); (Step 3) cyclizing the plasmid from which the stuffer DNA (X) has been removed; and (Step 4) cleaving the cyclized plasmid at the target sequence (Y) to obtain a linear splitting vector so as to introduce it into a homologous region of a yeast chromosome. It seems that by introducing the linear splitting vector into a yeast cell, homologous recombination occurs within the target sequence, and then the oppositely-oriented telomere sequences are resolved so as to split the chromosome.

However, in the above-described method, a complicated four step procedure is necessary, and in this method, the following time-consuming work is required: (1) it is necessary to clone the target sequence to the splitting vector for every splitting; (2) the vector used in Step 1 to which the target sequence Y is introduced and the vector used in Step 3 that is re-cyclized have to be introduced into bacterial cells for amplification; and (3) the target sequence is cleaved at only one site with a restriction enzyme in order to increase an efficiency of oriented integration at a homologous region. Thus, in this method, a plurality of complicated steps is required and it takes much time for the splitting of chromosome.

Therefore, it was attempted to split a chromosome by preparing a linear splitting vector (A) having a telomere sequence (i)—a centromere sequence of a yeast chromosome—a target sequence (i) in this order, and a linear splitting vector (B) having a target sequence (b)—a marker gene sequence—a telomere sequence (ii) in this order, and introducing them into a yeast. When these two linear splitting vectors were introduced into the yeast, splitting of yeast chromosome was confirmed. These two splitting vectors was obtained from a vector having a target sequence (δ)—CEN—a Tr sequence and a vector having a target sequence (δ)—a marker gene—a Tr sequence, as shown in FIG. 18A. Therefore, there is no need for complicated steps that are required in the conventional method using the chromosome splitting vectors, for example, as shown in FIG. 17.

However, the two splitting vectors could not be amplified by PCR (see FIG. 18C). PCR was performed in order to obtain linear splitting vectors (A) and (B) using a plasmid that contain Tr sequence as a template as shown in FIG. 18B. The PCR products 7 and 8 were analyzed and it was found that non-specific amplification had occurred as shown in FIG. 18C. One of the reasons why the two splitting vectors could not specifically be amplified by PCR is that there is a repetitive sequence of about 300 bp in the Tr sequence, as described above. For this reason, even with the method using the two splitting vectors, which is much simpler than the method shown in FIG. 17, an operation of amplifying and cleaving a cyclic vector and collecting DNA fragments still has to be performed to obtain the splitting vectors, which is still complicated.

Therefore, it is desirable to develop a simpler technique for manipulating, or isolation of the large size DNA such as, in particular, chromosomes, using a yeast as a host.

SUMMARY OF THE INVENTION

The object of the present invention is to provide a method for preparing a chromosome splitting vector easily and achieving chromosome modification, in particular, splitting and loss, and isolation of a chromosome.

The inventors of the present invention conducted in-depth research on a method for splitting a chromosome, in particular, a chromosome splitting vector that is used, and found that amplification of the chromosome splitting vector with PCR can be achieved when the number of repeat units of 5'-CCCCAA-3' is reduced to about ⅕ to ⅙ of that of the conventionally used Tr sequence, and that a chromosome splitting vector even with this short repeat units can serve as the Tr sequence and can split a yeast chromosome. Thus, the present invention has been achieved.

The present invention provides a method for modifying a chromosome in a yeast including preparing a linear chromosome splitting vector (1) having a target sequence (a), a marker gene sequence and $(C_4A_2)_n$ sequence (x) in this order; preparing a linear chromosome splitting vector (2) having a target sequence (b), a centromere sequence of a yeast chromosome and $(C_4A_2)_n$ sequence (y) in this order; and introducing the chromosome splitting vectors (1) and (2) into a yeast, wherein n is each independently an integer of 6 to 10.

In a preferable embodiment, the chromosome splitting vectors (1) and (2) are vectors obtained by PCR.

In a further preferable embodiment, n of both $(C_4A_2)_n$ sequences (a) and (b) is 6.

In a preferable embodiment, modification of chromosome is caused by splitting and/or loss of a yeast chromosome.

BRIEF DESCRIPTION OF THE DRAWINGS

FIGS. 2A to 2C are diagrams showing the manner in which a marker gene is deleted by a Cre-loxP system.

FIGS. 3A to 3C are schematic diagrams showing the splitting of a chromosome using the method of the present invention.

FIGS. 6A and 6B are schematic diagrams showing the manner in which splitting with a chromosome splitting vector occurs.

DESCRIPTION OF THE PREFERRED EMBODIMENT

The method for modifying a chromosome of the present invention uses two-chromosome splitting vector system including chromosome splitting vectors (1) and (2). The chromosome splitting vector (1) is linear and has a target sequence (a), a marker gene sequence and a $(C_4A_2)_n$ sequence (x) in this order. The chromosome splitting vector (2) is linear and has a target sequence (b), a centromere sequence of a yeast chromosome and a $(C_4A_2)_n$ sequence (y) in this order. The $(C_4A_2)_n$ in the chromosome splitting vectors (1) and (2) means a sequence in which a nucleotide sequence of 5'-CCCCAA-3', which is a repetitive sequence unit of the Tr sequence, is repeated n times, and n is each independently an integer of 6 to 10. Most preferably, both n are 6.

Figure 1:
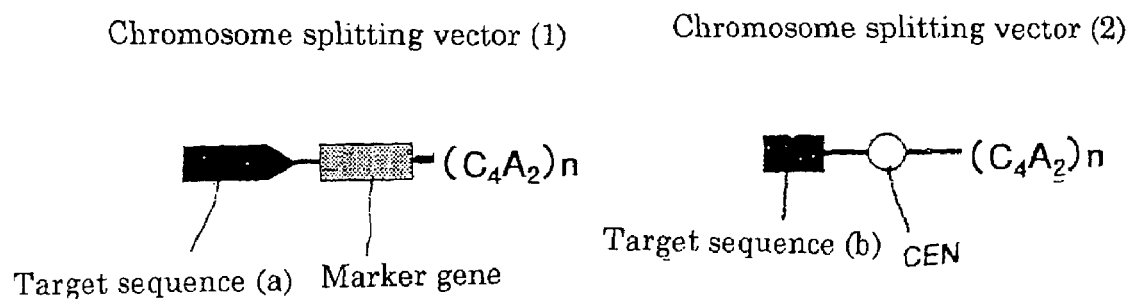
FIG. 1 is a schematic diagram of a chromosome splitting vector used in the present invention.

FIG. 1 shows the chromosome splitting vectors (1) and (2) used in the present invention. Although the two chromosome splitting vectors (1) and (2) have only 6 to 10 repetitive sequence units of 5'-CCCCAA-3', which is much less than in the conventionally used Tr sequence, they can function as a telomere sequence in yeast, so that a yeast chromosome can be split. Furthermore, the vectors can be amplified with PCR and thus can be prepared easily.

Centromere Sequence of a Yeast Chromosome

The centromere sequence of a yeast chromosome refers to a sequence necessary for mitosis of a yeast chromosome. The centromere sequence of any chromosome can be used without any particular limitation. In particular, CEN4 or CEN6 are preferably used. The centromere sequence of a yeast chromosome can be prepared easily with PCR using a plasmid having a desired centromere sequence (e.g., pDW26 (Windiant, D. et al, J Ferment, Bioeng, 82, 199-204 (1996)) as a template. In preparation, if a pair of primers including appropriate restriction enzyme cleavage sites is used, a DNA fragment including a desired centromere sequence can be recovered easily.

Marker Gene

There is no particular limitation regarding the marker gene, as long as it can monitor that a chromosome splitting vector has been introduced into yeast. In general, auxotrophic marker genes such as HIS3, HIS5, URA3, ADE2, LEU2, TRP1, and LYS2 can be used. A drug resistance marker gene that can be expressed in an eukaryote, for example, a kanamycin resistance gene (Km) can also be used. The sequence of a marker gene can be prepared easily with PCR, using a plasmid having the marker gene as a template. In preparation, if a pair of primers having appropriate restriction enzyme cleavage sites is used in the PCR amplification, a DNA fragment having a desired marker gene sequence can be recovered easily by digesting the PCR product by the restriction enzymes.

Target Sequence

The target sequence refers to a sequence in which a sequence of a splitting site of a chromosome (e.g., a yeast chromosome, a plant chromosome, an animal chromosome etc.) is included. The target sequence can be obtained by synthesizing the sequence corresponding to the splitting site of the chromosome. A DNA fragment having a desired target sequence can be prepared and recovered easily with PCR using the total DNA of yeast as a template, for example, using a pair of primers designed to add appropriate restriction enzyme cleavage sites.

Preparation of Chromosome Splitting Vector (1)

The chromosome splitting vector (1) is a linear vector having a target sequence (a), a marker gene sequence and a $(C_4A_2)_n$ sequence (x) in this order. The chromosome splitting vector (1) can be prepared by performing PCR, for example, using the $(C_4A_2)_n$ sequence and the target sequence (a) as a pair of primers, and a vector having an appropriate marker gene as a template.

The plasmid that can be used as a template of the chromosome splitting vector (1) can be constructed in the simplest manner, for example, as follows: PCR is performed with appropriate primers, using a plasmid in which a HIS3 gene derived from *Candida glabrata* (CgHIS3 gene) is introduced into pUC 18 (Kitada et al., (1995) Gene 165, 203-206) (this plasmid is referred to as "p1417" in this specification) as a template. The obtained DNA fragment (PCR product) containing the CgHIS3 gene is collected and inserted in pBluescript II SK+ (STRATAGENE).

When the chromosome splitting vector (1) having a marker gene is used, a resultant transformant having the split chromosome cannot be used as a host for subsequent transformations because the marker gene still remains. This means that sequential splitting of chromosome cannot be performed a plurality of times. If the marker gene contained in the transformant in which chromosome is split can be removed by some means after transformation, transformation (splitting of chromosomes) can be performed a plurality of times. If the sequential splitting of chromosome can be done, it is expected that information on or knowledge of the gene function, for example, the number, the length and the amount of chromosomes necessary for growth of yeast, can be obtained, and the function of the yeast chromosome can be analyzed. Consequently, useful yeast such as yeast having mini-chromosomes that are created based on the information and suitable for efficient production of a desired substance can be bred.

Therefore, it is preferable to use a system that can delete the selection marker so that the transfomant can be re-used as a host, which makes it possible to conduct the consecutive splitting of the chromosome. A site-specific recombination system (Cre-loxP system) can be used as the deletion system of the marker gene. Therefore, a plasmid having the marker gene in a Cre-loxP system can be preferably used as a template of the chromosome splitting vector (1) so that the marker gene can be removed after the transformation is completed. This Cre-loxP system is available in a plasmid pUG6 (Guldener et al. (1996) Nucleic Acids Res. 24(13), 2519-2524). FIGS. 2A to 2C show the Cre-loxP system. As shown in FIG. 2A, the marker gene is inserted in-between the loxP genes. Then, as shown in FIG. 2B, site-specific recombination occurs by the expression of the Cre recombinase, and as shown in FIG. 2C, the marker gene is removed by the Cre recombinase. The expression of the Cre recombinase is regulated by a promoter of a GAL1 gene encoding a galactose metabolizing enzyme.

The plasmid used as a template of the chromosome splitting vector (1) can be constructed by using the plasmid pUG6, for example, in the following manner: (i) PCR is performed, using the plasmid p1417 having the CgHIS3gene as a template so as to obtain a DNA fragment containing the CgHIS3gene: (ii) the thus-obtained DNA fragment is cloned into a pT7Blue-T vector (Novagen); (iii) the DNA fragment containing the CgHIS3 gene is cut out again, recovered, and inserted it into the plasmid pUG6 from which the kanamycin resistance gene has been removed; (iv) a DNA fragment containing the CgHIS3 gene is recovered from the obtained plasmid and inserted it into a pBluescript II SK+ (STRATAGENE). Thus, a plasmid (pUG6-CgHIS3: refer to FIG. 12) that can be used as a template of the chromosome splitting vector (1) can be obtained.

Figure 12:
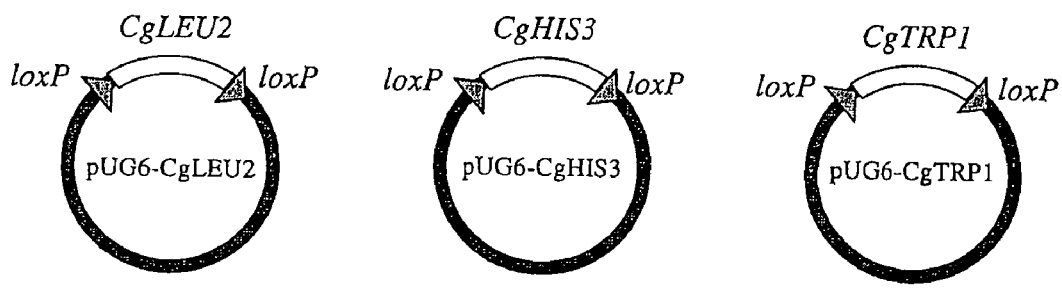
FIG. 12 is a schematic view of plasmids pUG6-CgHIS3, pUG6-CgLEU2 and pUG6-CgTRP1 that are used as templates for preparation of chromosome splitting vectors.

Plasmid pUG6-CgLEU2 or pUG-CgTRP can be obtained from a plasmid containing CgLEU2 gene or CgTRP1 gene, respectively, in the same manner as the above described. Refer to FIG. 12.

The plasmid containing the marker gene that is obtained through the steps of (i) to (iv) contains a selection marker gene in the site-specific recombination system (Cre-loxP system) as shown in FIGS. 2A to 2C that is derived from the plasmid pUG6. Using the Cre-loxP system, it becomes possible to split a chromosome consecutively in the same host. Therefore, PCR is performed, using a plasmid harboring the Cre-loxP system as a template, so as to include the marker gene sandwiched by the loxP genes. The thus obtained chromosome splitting vector (1) can be consecutively used for transformation in the same host.

The chromosome splitting vector (1) can be obtained by performing PCR with the plasmid having the marker gene as a template, using a primer having a target sequence (a1) having a homology to the area of the yeast chromosome to be split and a sequence (a2) homologous to the template plasmid, and a primer having a $(C_4A_2)_n$ sequence and a sequence (a3) homologous with the template plasmid. The sequences (a2) and (a3) having a homologous sequence with the template plasmid are selected so as to sandwich the marker gene sequence. There is no particular limitation on the conditions of the PCR and the conditions routinely used by those skilled in the art can be used.

Preparation of Chromosome Splitting Vector (2)

The chromosome splitting vector (2) is a linear vector having a target sequence (b), a centromere sequence of a yeast chromosome (CEN) and a $(C_4A_2)_n$ sequence (y) in this order. The chromosome splitting vector (2) is prepared by performing PCR, for example, using a vector having a centromere sequence of a yeast as a template, and the $(C_4A_2)_n$ sequence and the target sequence (b) as primers.

The plasmid used as a template of the chromosome splitting vector (2) can be constructed, for example, in the following manner. PCR is performed with an appropriate primer, using a chromosomal DNA of yeast as a template; then, the obtained DNA fragment is cloned into pT7Blue-T vector (Novagen); and the DNA fragment containing centromere sequence (for example, CEN4) is recovered with an appropriate restriction enzyme and is inserted into pBluescript II SK+ (STRATAGENE). Thus, the plasmid that can be used as a template of the chromosome splitting vector (2) can be obtained.

The chromosome splitting vector (2) can be obtained by performing PCR using the plasmid having the yeast centromere as a template, using a primer having a target sequence (b1) that has a homology with a site of the yeast chromosome to be split and a sequence (b2) homologous with the template plasmid, and a primer having a $(C_4A_2)_n$ sequence and a sequence (b3) homologous with the template plasmid. The sequences (b2) and (b3) having a homologous sequence with the template plasmid are selected so as to sandwich the yeast centromere sequence.

Method for Splitting a Yeast Chromosome

The method of the present invention will be described schematically with reference to FIGS. 3A to 3C by taking an example in which the $(C_4A_2)_6$ sequence is used as a primer. First, as shown in FIG. 3A, the chromosome splitting vectors (1) and (2) are prepared using a sequence having a target sequence (a) or a target sequence (b) and a $(C_4A_2)_6$ sequence as a primer, and using a plasmid having a marker gene (M) or a centromere sequence (CEN4). Then, as shown in FIG. 3B, the chromosome splitting vectors (1) and (2) are introduced into yeast. It seems that the introduced chromosome splitting vectors cause homologous recombination at a homologous site of the yeast chromosome, and thus the chromosome splitting vectors (1) and (2) are inserted into the yeast chromosome. Then, as shown in FIG. 3C, the telomere sequence of the yeast appears to be added to the $(C_4A_2)_6$ sequence, which provides the function as a chromosome. The orientation of the target sequence (a) and (b) in the primers is designed so that each of the $(C_4A_2)_6$ sequences in the splitting vectors (a) and (b) becomes a terminal of each two split chromosomes when telomere resolution occurred.

Splitting and/or Loss of a Yeast Chromosome

Figure 4A:
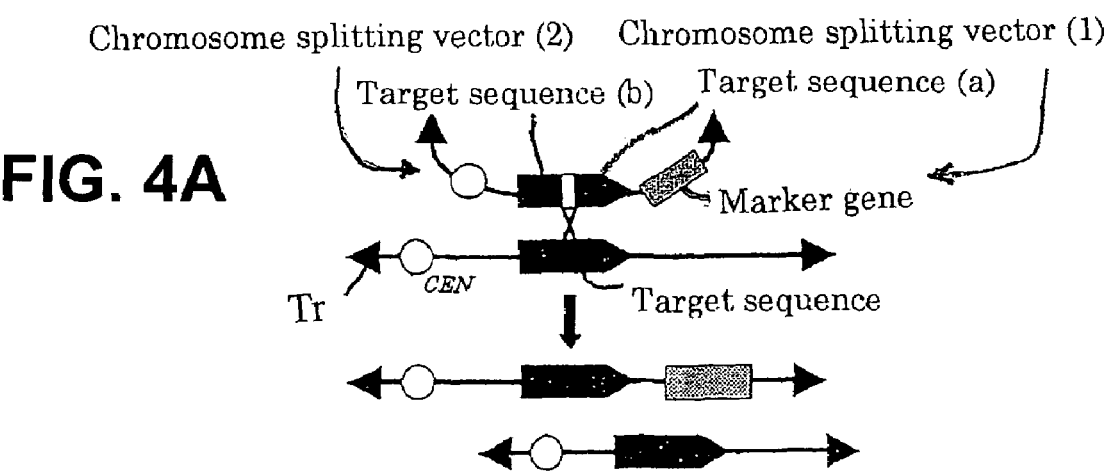
FIGS. 4A to 4C are schematic diagrams showing the manner in which the splitting and the loss occur in a yeast chromosome.
Figure 4B:
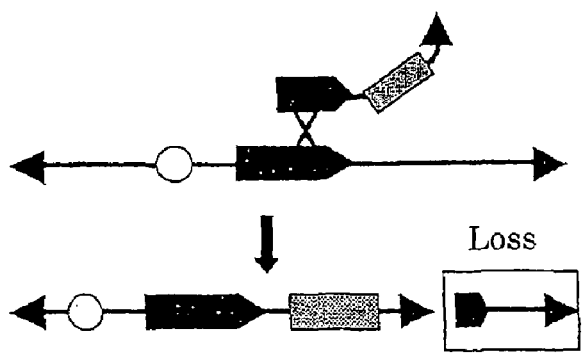
Figure 4C:
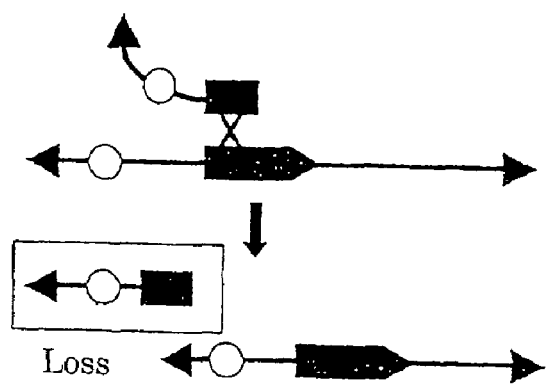

Splitting and/or loss of a yeast chromosome using the chromosome splitting vectors of the present invention will be described. When a chromosome is split, there are cases in which a loss in the chromosome occurs and cases in which it does not occur. FIGS. 4A to 4C show the manner in which splitting and/or loss occurs in a chromosome. For example, in FIG. 4A, the target sequences (a) and (b) are constituted in such a manner that, sandwiching the splitting site, the target sequence (b) has the chromosome sequence on the left side of the splitting site, and the target sequence (a) has the chromosome sequence on the right side of the splitting site. It seems that the linear chromosome splitting vectors (1) and (2) having such target sequences (a) and (b), respectively, are introduced into a yeast simultaneously, so that the chromosome can be split as shown in the lowest stage in FIG. 4A.

It is also possible that the chromosome splitting vector (1) or (2) alone participates in splitting or loss, as shown in FIGS. 4B and 4C. It seems that splitting or loss of a chromosome occurs in the manners shown in FIGS. 4A to 4C alone or in combination, or in another manner.

Furthermore, when the obtained transformant having the split chromosomes includes the site-specific recombination system (Cre-loxP system), it is possible to remove the marker gene by expressing the Cre enzyme so that the chromosome splitting vectors having the same marker can be subsequently introduced into the transfomant having the split chromosomes.

EXAMPLES

Hereinafter, the present invention will be described by way of examples, but the present invention is not limited to the examples.

Conditions of PCR

In the following reference examples and working examples, amplification of DNA fragments with PCR and preparation of the chromosome vectors (1) and (2) were performed under the following conditions.

First, 0.2 µl of Takara Ex Taq DNA polymerase (Takara Shuzo Co. Ltd), 4 µl of 10×Reaction buffer (Takara Ex Taq DNA polymerase buffer), 4 µl of dNTP mixed solution (2.5 mM each of dATP, dTTP, dGTP, and dCTP), 0.2 µl of the template DNA, and 2 µl each of two types of primer DNA (20 pmol/µl each) were put in a 0.2 ml tube for this purpose and were diluted to 40 µl with a sterile water. The mixture was placed in a GeneAmp PCR System (PERKIN ELMER) and reactions at (1) 94° C. for three minutes; (2) 94° C. for one minute (denaturation of double stranded DNA); (3) 50 to 60° C. for 2 minutes (annealing of primers); (4) 72° C. for 1 to 3 minutes (elongation of DNA with polymerase); and (5) 4° C. for 10 minutes are repeated 25 times.

Yeast to be Used and Chromosome to be Split

Chromosome I (230195 bp), which was the smallest of the 16 chromosomes of a haploid budding yeast, was used as the chromosome to be split. The CgHIS3 gene was used as the selection marker, and the splitting site was set approximately at a center of chromosome I (between 119874 bp and 119875 bp). If the chromosome I is split as desired, chromosome I should be split to about 120 kbp and about 110 kbp. The haploid budding yeast is a SH5209(a) strain (formerly FY833 strain: MATa his3Δ200 ura3-52 leu2Δ1 lys2Δ202 trpl Δ63 (Winston et al. (1995) Yeast 11, 53-55).

Reference Example 1

Construction of a Plasmid pSK+CgHIS3 as a Template for Construction of the Chromosome Splitting Vector (1)

A plasmid pSK+CgHIS3 is obtained by incorporating a CgHIS3 gene, which is incorporated into loxP sites of a Cre-loxP system, into pBluescript II SK+ (STRATAGENE).

First, PCR was performed, using primers CgHIS3-1 and CgHIS3-2 having the following sequences, and a plasmid p1417 having a CgHIS3 gene as a template.

CgHIS3-1: 5'-CTCTCTAGATAACACCGATCAGATGCACA-3' (Sequence ID No. 1)

CgHIS3-2: 5'-CTCCTCGAGAAACTTGCTCTGCTAACTCA-3' (Sequence ID No. 2)

The obtained DNA fragment of about 1.62 kbp was cloned into pT7Blue-T vector (Novagen) with T4DNA ligase to construct a plasmid pT7-CgHIS3. The primer CgHIS3-1 has a sequence that generates a restriction enzyme XbaI cleavage site. Similarly, the primer CgHIS3-2 has a sequence that generates a restriction enzyme XhoI cleavage site.

Then, the plasmid pT7-CgHIS3 was digested with a restriction enzyme XbaI/XhoI. A DNA fragment of about 1.62 kbp containing the CgHIS3 gene was recovered, using GENE CLEAN II KIT (Funakoshi Co. Ltd.), from agarose gel. Then, plasmid pUG6 was digested with BglII/XhoI and Xba/XhoI to remove about 1.54 kbp including a kanamycin resistant gene. A DNA fragment without kanamycin resistant gene was recovered from the agarose gel, using GENE CLEAN II KIT (Funakoshi Co. Ltd.). Then, the DNA fragment of about 1.62 kbp containing the CgHIS3 gene was inserted into the XbaI/XhoI cleavage site of the recovered DNA fragment, so that a plasmid pUG6-CgHIS3 was constructed.

CEN4-1: 5'-CTCGAATTCGGCCATTCTCATGAAGAATA-3' (Sequence ID No. 3)

CEN4-2: 5'-CTCGAATTCTCTAAGAGGTGATACTTATT-3' (Sequence ID No. 4)

The obtained DNA fragment of about 0.85 kbp was cloned into pT7Blue-T vector (Novagen) with T4DNA ligase to construct a plasmid pT7-CEN4. Each primer CEN4-1 and CEN4-2 has a sequence that generates a restriction enzyme EcoRI cleavage site, respectively.

Then, the obtained pT7-CEN4 was digested with a restriction enzyme EcoRI, and the DNA fragment of about 0.85 kbp containing the CEN4 was recovered. This 0.85 kbp DNA fragment was inserted into an EcoRI site of pBluescript II SK+ (STRATAGENE), so that a plasmid pSK+CEN4 was constructed.

Example 1

Production of a Chromosome Splitting Vector

Figure 5:
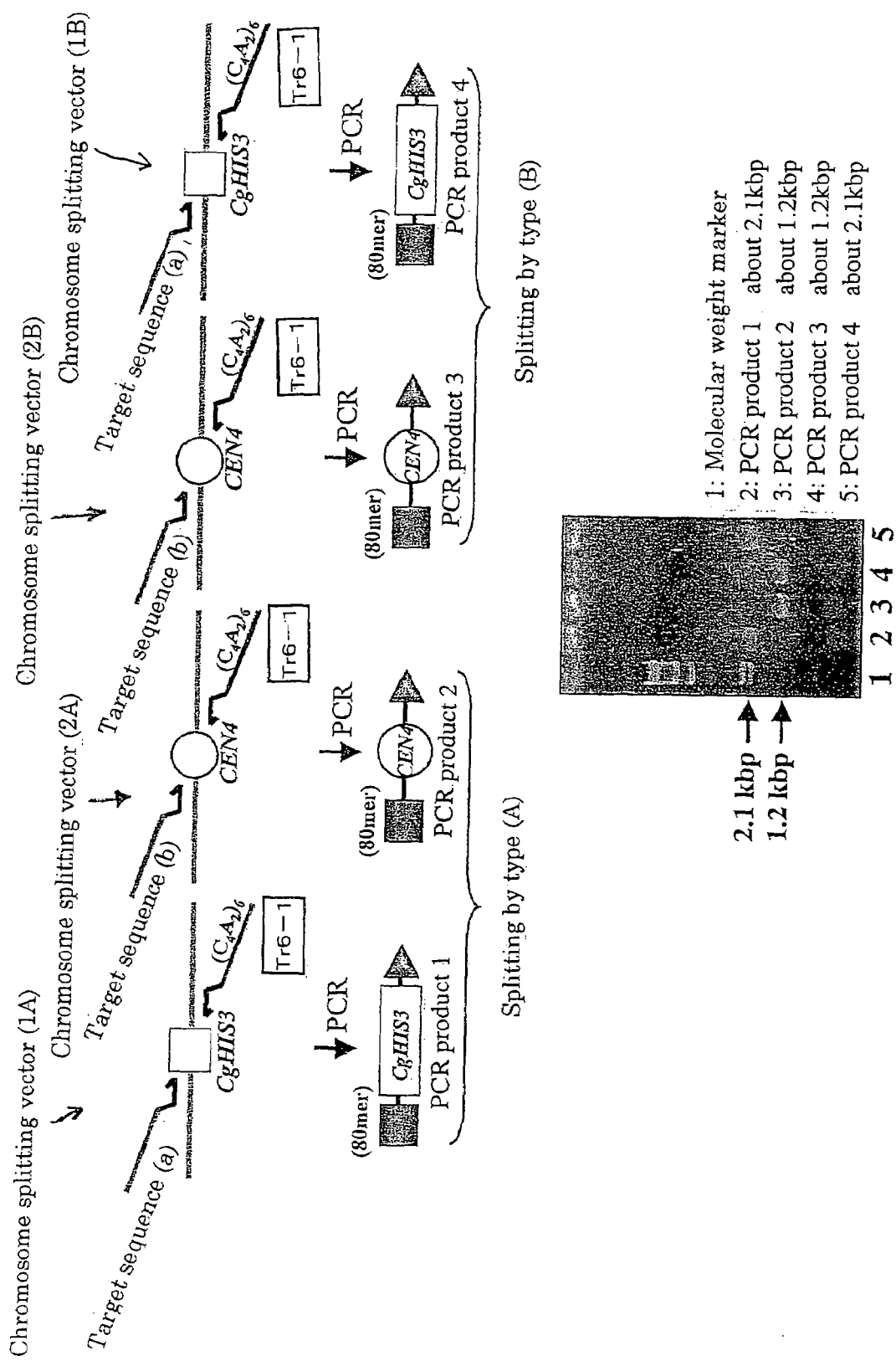
FIG. 5 is a schematic diagram showing the preparation of a chromosome splitting vector using PCR and a photograph of a gel electrophoresis of the PCR products.

FIG. 5 is a schematic diagram showing production of chromosome splitting vectors (1A), (2A), (1B) and (2B).

Production of Chromosome Splitting Vector (1A)

The following primers were used:

```
chIY-11: 5'-GAATGCTATGTTGTGGTTAGCGACCTGCCCCTTGCCAAATCTA    (Sequence ID No. 5)
TATCACCACTTCCTTAGCATGTAATCATTTACTTAAAGGAAACAGCTATGACCATG-3', and Tr6-1: 5'-CCCCAACCCCAACCCCAACCCCAACCCCAACCCCAATCGAGGT    (Sequence ID No. 6)
CGACGGTATCGAT-3'.
```

Then, the plasmid pUG6-CgHIS3 was digested with NotI to obtain about 1.79 kbp fragment containing the CgHIS3 gene. This 1.79 kbp fragment was inserted into a NotI site of pBluescript II SK+ (STRATAGENE), so that a plasmid pSK+CgHIS3 was constructed.

Reference Example 2

Construction of a Plasmid pSK+CEN4 as a Template for Constructing the Chromosome Splitting Vector (2)

A plasmid pSK+CEN4 is a plasmid having a centromere sequence of a yeast, and is used as a template for constructing the chromosome splitting vector (2). In this plasmid, a CEN4 gene is incorporated into pBluescript II SK+ (STRATAGENE) as centromere.

First, PCR was performed, using CEN4-1 and CEN4-2 having the following sequences as primers, and a chromosomal DNA of a wild-type budding yeast strain S288C as a template.

The primer chIY-11 (Sequence ID No.5) has 99bases. The 80 bases from the 5' terminal of the chIY-11 constitute a region homologous to the nucleotide sequence of 119795 bp to 119874 bp of chromosome I, which is the target sequence. The remaining 19 bases constitute a region homologous to the plasmid pSK+CgHIS3. The primer Tr6-1 has the $(C_4A_2)_6$ sequence and 20-base sequence homologous to sequences of the plasmid pSK+CgHIS3. PCR was performed using these two primers, and the plasmid pSK+CgHIS3 as a template, and thus a PCR product 1 (chromosome splitting vector (1A)) was obtained.

Production of chromosome splitting vector (2A)

The following primers were used:

```
chIY-12: 5'-GTTGAAAAGGAAATCAACGTTACAAAGTGCAGTTTTTTGTA    (Sequence ID No. 7),
TTATTTTCCTATTATCCTCTTCTTTTCCTTTGTTTCAGGGGAAACAGCTATGACCATG-3', and Tr6-1.                                                       (Sequence ID No. 6)
```

The primer chIY-12 (Sequence ID No.7) has 99bases. The 80 bases from the 5' terminal of the chIY-12 constitute a region homologous to the nucleotide sequence of 119875 bp to 119754 bp in chromosome I, which is the target sequence, and The remaining 19 bases constitute a region homologous to the plasmid pSK+CEN4. PCR was performed using these two primers, and the plasmid pSK+CEN4 as a template, and thus a PCR product 2 (chromosome splitting vector (2A)) was obtained.

Production of Chromosome Splitting Vector (2B)
The following primers were used:

```
chIY-13:  5'-TTTAAGTAAATGATTACATGCTAAGGAAGTGGTGAATAAGAT   (Sequence ID No. 8)
TTGGCAAGGGGCAGGTCGCTAACCACAACATAGCATTCGGAAACAGCTATGACCATG-3'
``` and primer Tr6-1.                                          (Sequence ID No. 6)

The primer chIY-13 (Sequence ID No.8) has 99bases. The 80 bases from the 5' terminal of the chIY-13 constitute a region homologous to the nucleotide sequence of 119795 bp to 119874 bp in chromosome I, which is the target sequence, and The remaining 19 bases constitute a region homologous to the plasmid pSK+CEN4. PCR was performed using these two primers, and the plasmid pSK+CEN4 as a template, and thus a PCR product 3 (chromosome splitting vector (2B)) was obtained.

Production of Chromosome Splitting Vector (1B)
The following primers were used:

```
chIY-14:  5'-CCTGAAACAAAGGAAAAGAAGAGGATAATAGGAAAATAATA   (Sequence ID No. 9)
CAAAAAACTGCACTTTGTAACGTTGATTTCCTTTTCAACGGAAACAGCTATGACCATG-3'
``` and primer Tr6-1                                           (Sequence ID No. 6)

The primer chIY-14 (Sequence ID No.9) has 99bases. The 80 bases from the 5' terminal of the chIY-13 constitute a region homologous to the nucleotide sequence of 119875 bp to 119754 bp in chromosome I, which is the target sequence, and The remaining 19 bases constitute a region homologous to the plasmid pSK+CgHIS3. PCR was performed using these two primers, and the plasmid pSK+CgHIS3 as a template, and thus a PCR product 4 (chromosome splitting vector (1B)) was obtained.

FIG. 5 shows a photograph of a gel electrophoresis of the PCR products 1 to 4. Fragments having a size of about 2.1 kbp are amplified specifically (PCR products 1 and 4), and fragments having a size of about 1.2 kbp are amplified specifically (PCR products 2 and 3). Thus, it is evident that specific amplification can be achieved by PCR using the repetitive sequence of $(C_4A_2)_6$ as the primers. This confirms that the chromosome splitting vectors (1) and (2) can be prepared by PCR.

The obtained chromosome splitting vectors (1A) and (2A) perform splitting of a chromosome in a manner that each of target sequences is introduced into each split chromosomes (hereinafter, referred to as "type (A)"), as shown in FIG. 6A. The chromosome splitting vectors (1B) and (2B) perform splitting of a chromosome in a manner that a target sequence is not introduced into each split chromosomes (hereinafter, referred to as "type (B)"), as shown in FIG. 6B.

Example 2

Splitting of a Yeast Chromosome -1

A pair of the chromosome splitting vectors (1A) and (2A) or the chromosome splitting vectors (1B) and (2B) obtained by the above-described PCR were transformed into a yeast strain SH5209 by the lithium acetate method. Transformants (yeast in which chromosome I was expected to be split as desired) that can grow on a His-deficient medium were selected. When the splitting of type A was performed using the chromosome splitting vectors (1A) and (2A), six transformants were obtained. When the splitting of type B was performed using the chromosome splitting vectors (2B) and (1B), four transformants were obtained.

Figure 7:
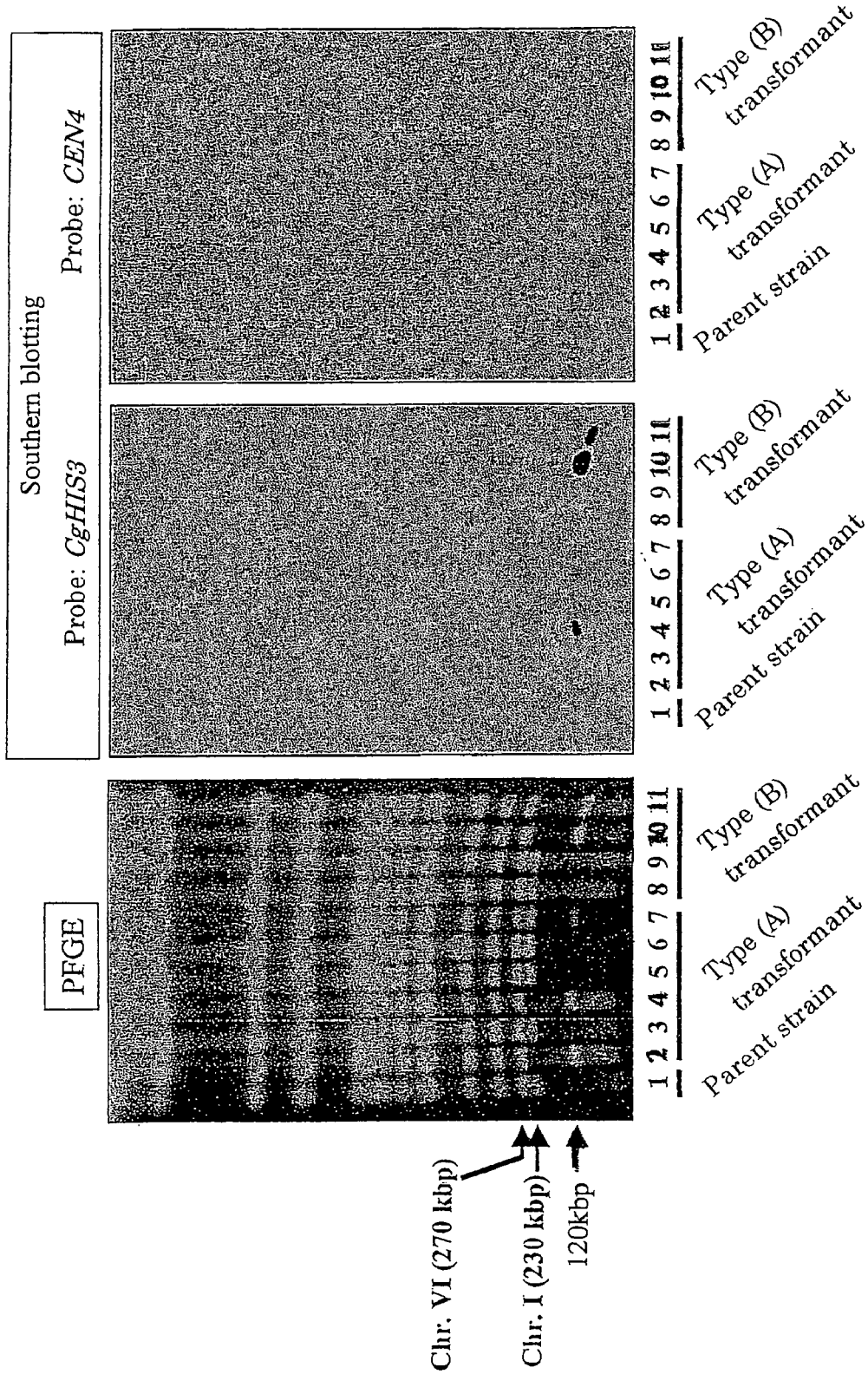
FIG. 7 shows a photograph of a pulse field gel electrophoresis (PFGE) and Southern blotting of the chromosomes of the transformants.

Then, in these transformants, a pulse field gel electrophoretic (PFGE) analysis and a Southern blotting were performed in order to investigate whether chromosome I had been split as desired (FIG. 7). If being split as desired, chromosome I should be split into about 120 kbp and about 110 kbp. As a result of the PFGE analysis, the band of chromosome I would disappear and a new band would be generated in the vicinity of 120 kbp in two transformants (lanes 2 and 4 in FIG. 7) in the splitting of type (A), and also in two strains (lanes 10 and 11 in FIG. 7) in the splitting of type (B). If being split as desired, chromosome I should be split into two fragments of about 120 kbp and about 110 kbp, but it seems that the two bands overlap each other in the vicinity of about 120 kbp. Then, a Southern blotting was performed. As a result, in both the analysis using CgHIS3 as a probe that should be incorporated in the split chromosome of about 110 kbp and the analysis using CEN4 as a probe that should be incorporated in the split chromosome of about 120 kbp, signals were obtained in the vicinity of 120 kbp in the lanes 2, 4, 10 and 11. Therefore, the split chromosome (about 110 kbp) containing CgHIS3 and the split chromosome (about 120 kbp) containing CEN4 overlap each other, which indicates that in the transformants of the lanes 2, 4, 10 and 11, chromosome I was split as desired.

In the analysis using CEN4 as a probe, chromosome IV was detected in none of the lanes. Because chromosome IV is very large (about 1.5 Mbp), chromosome IV could not be transferred onto a membrane for the Southern blotting. In the transformants in lanes 5, 6, 8 and 9, chromosome I did not appear to be split. From the result of Southern blotting analysis using CgHIS3 as a probe, it is believed that the CgHIS3 gene was introduced into another chromosome than chromosome I, and therefore these strains were able to grow on a His-deficient medium.

In the transformant in lane 7, chromosome I was not split, however, this transformant was able to grow in a His-deficient medium. This is most probably because the transformant had the split chromosome (about 110 kbp) containing CgHIS3 in a newly generated split chromosome. Summing up these results, chromosome I of a yeast was split at a frequency of ⅓ in the splitting vector of type (A) and a frequency of ½ in the splitting vector of type (B), and therefore, there is substantially no difference between the two types (A) and (B) splitting. Thus, it is evident that the chromosome can be split at a high frequency using two chromosome splitting vectors that has been prepared with PCR in a simple manner.

Example 3

Construction of Chromosome Splitting Vectors (1C) and (2C)

Construction of Chromosome Splitting Vector (1C)

Figure 8:
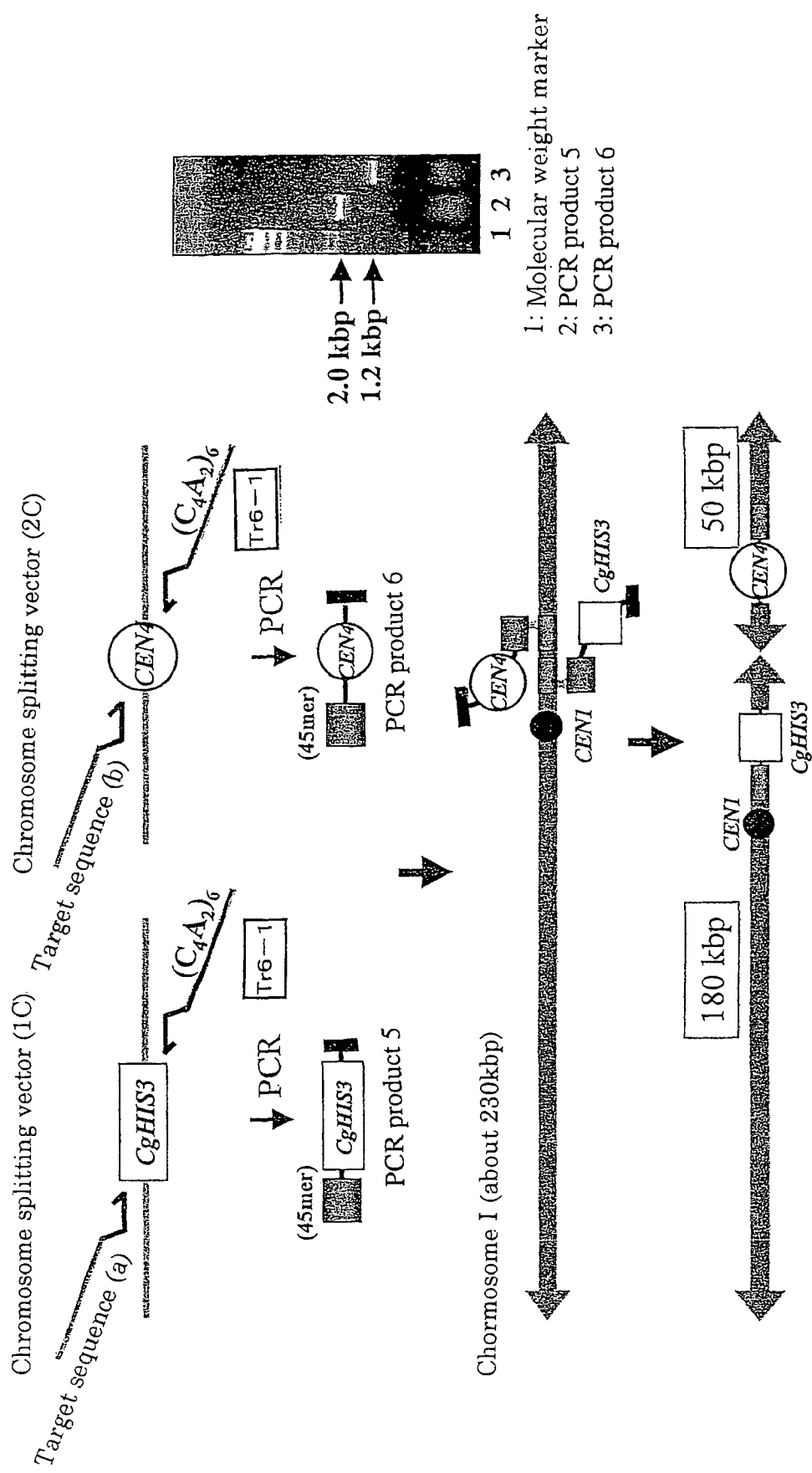
FIG. 8 is a schematic diagram showing the preparation of a chromosome splitting vector using PCR and a photograph of a gel electrophoresis of the PCR products.

FIG. 8 shows a schematic diagram for construction of chromosome splitting vector (1C).

The following primers:

chIY-15: 5'-CAAGAAATATCTTGACCGCAGTGAACTGTGGGAATA (Sequence ID No. 10)
CTCAGGTATACAGCTATGACCATG-3' and Tr6-1 were used.　　　　　　　　　　(Sequence ID No. 6)

The primer chIY- 15 (Sequence ID No. 10) has 60 bases. The 45 bases from the 5' terminal of the chIY-15 constitute a region homologous to the nucleotide sequence of 181165 bp to 181209 bp in chromosome I, which is the target sequence, and The remaining 15 bases constitute a region homologous to the plasmid pSK+CgHIS3. PCR was performed using these two primers, and the plasmid pSK+CgHIS3 as a template, and thus a PCR product 5 (chromosome splitting vector (1C)) was obtained.

Construction of Chromosome Splitting Vector (2C)

FIG. 8 shows a schematic diagram for construction of chromosome splitting vector (2C).

The following primers:

chIY-16: 5'-GAAAAAATAATGGTTGCTAAGAGATTCGAACTCTTGCATCT (Sequence ID No. 11)
TACGACAGCTATGACCATG-3' and Tr6-1 were used.　　　　　　　　　　(Sequence ID No. 6)

PCR was performed using the plasmid pSK+CEN4 as a template. The primer chIY- 16 (Sequence ID No.11) has 60 bases. The 45 bases from the 5' terminal of the chIY- 16 constitute a region homologous to the nucleotide sequence of 181210 bp to 181254 bp in chromosome I, which is the target sequence, and The remaining 15 bases constitute a region homologous to the plasmid pSK+CEN4. PCR was performed using these two primers, and the plasmid pSK+CEN4 as a template, and thus a PCR product 6 (chromosome splitting vector (2C)) was obtained.

A photograph of a gel electrophoresis of the PCR products 5 and 6 is shown in FIG. 8. Fragments having a size of about 2.0 kbp and about 1.2 kbp are amplified specifically, which confirms that the chromosome splitting vectors (1C) and (2C) were obtained.

The obtained chromosome splitting vectors (1C) and (2C) are vectors for type (B) splitting of chromosomes shown in FIG. 6B. When being split as desired, chromosome I should be split between the 181209 bp and 181210 bp, and into about 180 kbp and about 50 kbp fragments.

Example 4

Splitting of Yeast Chromosome -2

A pair of the chromosome splitting vectors (1C) and (2C) were introduced into a yeast strain SH5209 by the lithium acetate method. Transformants that can grow on a His-deficient medium were selected. Since a large number of transformants were obtained, 24 tranformants were selected at random and were subjected to PFGE.

Figure 9:
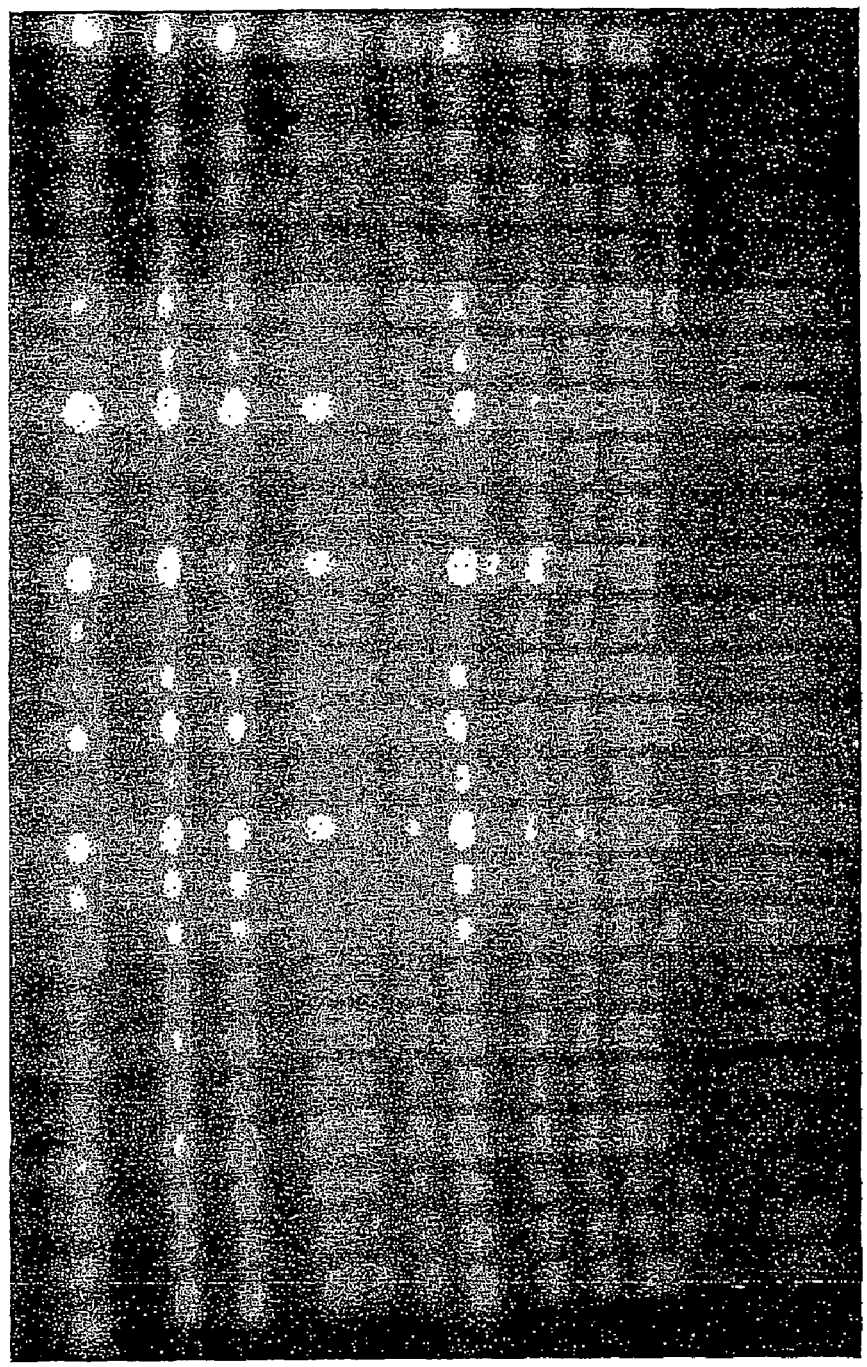
FIG. 9 shows a photograph of a pulse field gel electrophoresis (PFGE) and Southern blotting of the chromosomes of the transformants.
Figure 10:
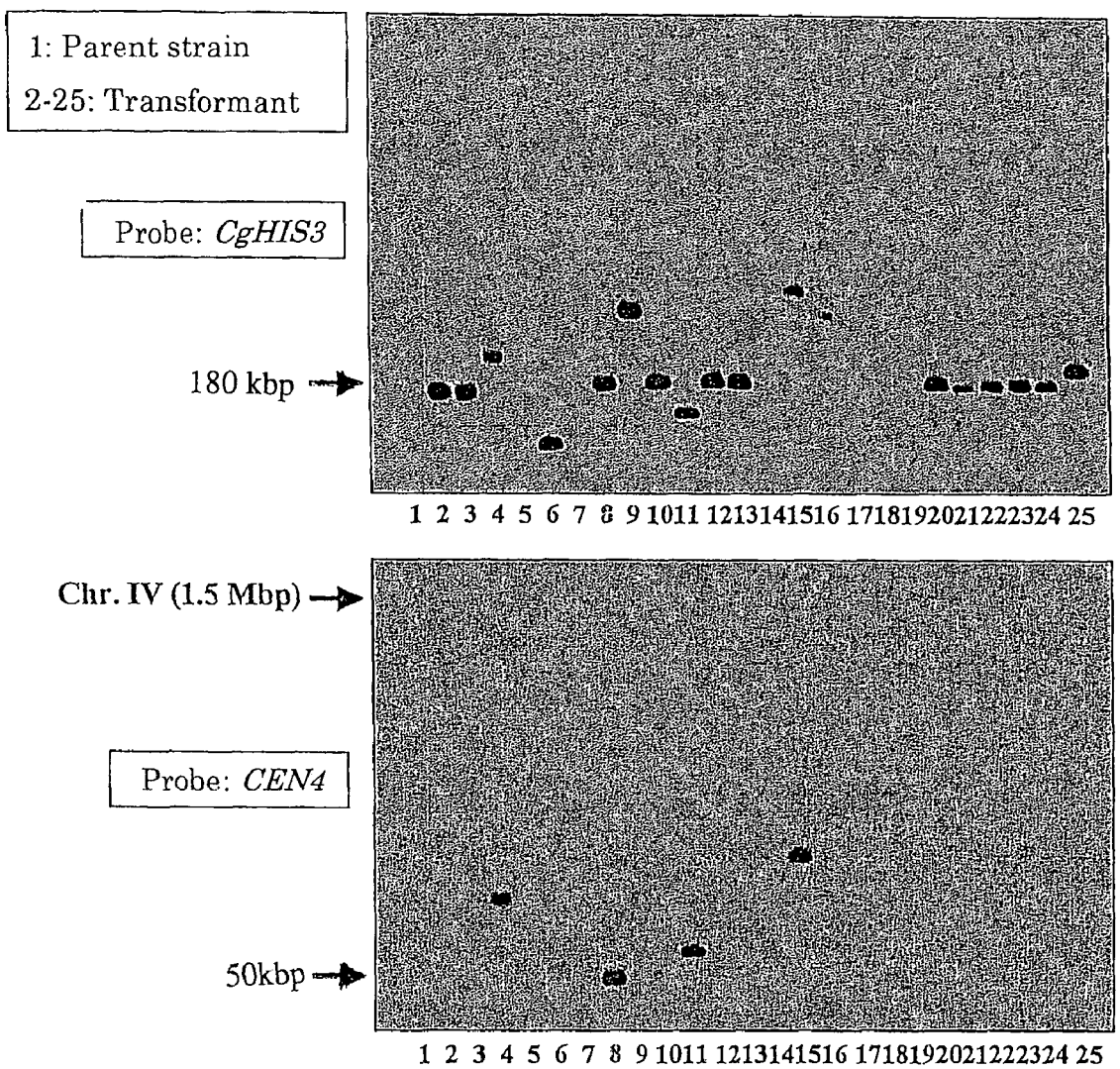
FIG. 10 shows photographs showing the Southern blotting of the PFGE of FIG. 9.

FIG. 9 shows the results. The band of chromosome I of the transformant of a lane 8 has disappeared, and two new bands have been generated in the vicinity of 180 kbp and 50 kbp, respectively. Then, the Southern blotting was performed for in-depth examination (FIG. 10). As a result, in the transformant of the lane 8, a signal was obtained in the vicinity of 180 kbp in the analysis using CgHIS3 as a probe, and a signal was obtained in the about 50 kbp in the analysis using CEN4 as a probe. These results indicate that in the transformant of the lane 8, chromosome I was split into two chromosomes of about 180 kbp and about 50 kbp, as desired. Therefore, also in a splitting using a homologous region of 45 mer, chromosome I can be split as desired as a frequency of 1/24.

Compared with the splitting in the central region of chromosome I (Working Example 2), an incidence of the transformants in which splitting has occurred was low in Working Example 4, possibly due to the three following reasons: 1) the splitting efficiency varies significantly depending upon the structure of a site to be split; 2) the length of the homologous region to chromosome is decreased about 50% from 80 bases to 45 bases; and 3) a gene necessary for growth (hereinafter, referred to as "essential gene") was not distributed to a split chromosome in this splitting.

No essential gene is present in the obtained split chromosome of about 50 kbp. Therefore, even if recombination occurs with the chromosome splitting vector (1C) having CgHIS3, it is not necessary that recombination occurs with the chromosome splitting vector (2C) having CEN4. However, in the splitting at the central portion in chromosome I, the essential gene is distributed to the split chromosome, so that when recombination occurs only with a chromosome splitting vector (1C) having CgHIS3, this essential gene is lost, and therefore the transformant cannot survive. Therefore, in the splitting at about 50kbp of the right arm of chromosome I that is not involved in the distribution of the essential gene (splitting in Working Example 4), the number of quasi-positive transformants (lanes 2, 3, 21, 22, 23, 24 etc.) that grew on a His-deficient medium is larger than that in the splitting in the central portion of chromosome I that is involved in the distribution of the essential gene. As a result, the yield of the transformant having split chromosomes appears to be decreased. Alternatively, it is also possible that chromosome I of these quasi-positive transformants were split into two split chromosomes of about 180 kbp and about 50 kbp as desired, but since there is no essential gene in the split chromosome of about 50 kbp, the split chromosome of about 50 kbp is lost during cultivation. However, in either case, even if the fragment with a 45 base homologous region was used, a transformant in which the chromosome was split was obtained.

Example 5

Sequential Splitting of Yeast Chromosome

It was attempted to split chromosome I (230 kbp) sequentially into five fragments (45, 65, 25, 45, and 50 kbp) using the transformant in the lane 8 obtained in Example 4 (hereinafter, referred to as "transformant 8") as the parent strain.

Hereinafter, first, (A) preparation of oligonucleotide primers for PCR and (B) preparation of plasmids to be used will be described, and then (C) the results of preparing chromosome splitting vectors (1) and (2) with PCR and splitting the chromosome will be described.

A. Preparation of Oligonucleotide Primers for PCR

The primers used for isolation of a gene and preparation of chromosome splitting vectors are shown below. The synthesis of the primers was entrusted to Hokkaido System Science CO., LTD. The Sequence ID Nos. 12 to 13 are primers for preparing the chromosome splitting vector (1), and the underlined portion indicates restriction enzyme cleavage site given in parentheses. The Sequence ID Nos. 14 to 19 are 99-mer primers for preparing the chromosome splitting vector (2). The 80 bases from the 5' terminal of the primer constitute a region homologous to chromosome I of yeast, and the positional information of chromosome I is given in parentheses. The underlined 19 mers of the Sequence ID Nos. 14 to 19 show a region homologous to the plasmid used as a template. The Sequence ID No. 20 is a primer including $(C_4A_2)_6$ for preparing the chromosome splitting vectors (1) and (2), and the underlined 20 mers show a region homologous to the plasmid used as a template.

```
CEN4-1S:  5'-CTCGTCGACGGCCATTCTCATGAAGAATA-3'          (Sequence ID No. 12)
(SalI)

CEN4-2X:  5'-CTCCTCGAGTCTAAGAGGTGATACTTATT-3'         (Sequence ID No. 13)
(XhoI)

chI27:  5'-GGTCTTCATCCTCCATTTGGTCAATGCGGCCAACAATACGGATT  (Sequence ID No. 14)

TCCTCCTCATTGGAGCGCAGAGACCCTAACAACACACTTCGTACGCTGCA

GGTCG-3'

(Chromosome I 109496bp-109575bp)
chI28:  5'-TGTGTGGTCATGTTCAGCGTGAGCAAAATCAGTCGGAAAGTGA    (Sequence ID No. 15)

ACGAGAATTGGAATGTGGAAGACGGACATATCACTGACTTCGTACGCTG

CAGGTCG-3'

(Chromosome I 109576bp-109655bp)
chI29:  5'-TTATAATGAGCAAGTCGATACAAGGACTGCCCATAAAGTGGG     (Sequence ID No. 16)

AGGAGTACGCCGCTGATGAAGTGGTTTTGCTGGTACCTCTTCGTACGCTG

CAGGTCG-3'

(Chromosome I 42367bp-42446bp)
chI30:  5'-TATATGATTTTGTGTTCGTTTTTCGTCTTGCGAAAGGCATCCCC   (Sequence ID No. 17)

AATGGCTTGTTTCATTGATCCATCAGTGTGGCTCGTCTTCGTACGCTGCAG

GTCG-3'

(Chromosome I 42447bp-42526bp)
chI31:  5'-GACCAGTGAAGAGGAATTGAATAAGTAGAACTTGGGCAATAC     (Sequence ID No. 18)

TTATAACGGCAATGATAATGATAATCAATATAGATAACCTTCGTACGCTG

CAGGTCG-3'

(Chromosome I 137720bp-137799bp)
chI32:  5'-ACGAAGACTTTGAACTATTTGAGAGCCAGAGAATGGAGAAAC     (Sequence ID No. 19)

ATGTCTACCGTCAATTCCACCGAATCAAGGTTGACTTGCTTCGTACGCTG

CAGGTCG-3'

(Chromosome I 137800 bp-137879 bp)
Tr6-4:  5'-CCCCAACCCCAACCCCAACCCCAACCCCAACCCCAAGGCCA     (Sequence ID No. 20)

CTAGTGGATCTGAT-3'
```

B. Construction of Plasmids

B-1. Construction of Plasmid pT7-CEN4 (S/X)

Using primers CEN4-1S (Sequence ID No.12) and CEN4-2X (Sequence ID No.13) and a chromosomal DNA of a wild type budding yeast strain S288C as a template, PCR was performed and a DNA fragment of about 0.85 kbp was obtained and cloned into pT7Blue-T vector (Novagen), using T4 DNA ligase to construct a plasmid pT7-CEN4(S/X).

B-2. Construction of Plasmid pUG6-CEN4

Figure 11:
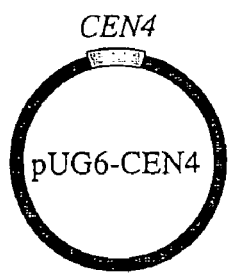
FIG. 11 is a schematic view of a plasmid pUG6-CEN4.

The plasmid pT7-CEN4(S/X) obtained in B-1 was digested with XhoI/SmaI, and a DNA fragment of about 0.85 kbp containing CEN4 was recovered from an agarose gel with GENE CLEAN II KIT (Funakoshi Co. Ltd.). Then, plasmid pUG6 (Güldener et al., (1996) Nucleic Acids Res. 24(13), 2519-2524) was digested with SalI/EcoRV, and a fragment that did not contain a kanamycin resistant gene was recovered from the agarose gel with GENE CLEAN II KIT (Funakoshi Co. Ltd.). Then, the DNA fragment of about 0.85 kbp containing CEN4 was inserted into the SalI/EcoRV site of the recovered fragment of the pUG6 to construct a plasmid pUG6-CEN4 (FIG. 11).

B-3. Construction of Plasmids pUG6-CLCEN4, pUG6-CHCEN4 and pUG6-CTCEN4

Figure 13:
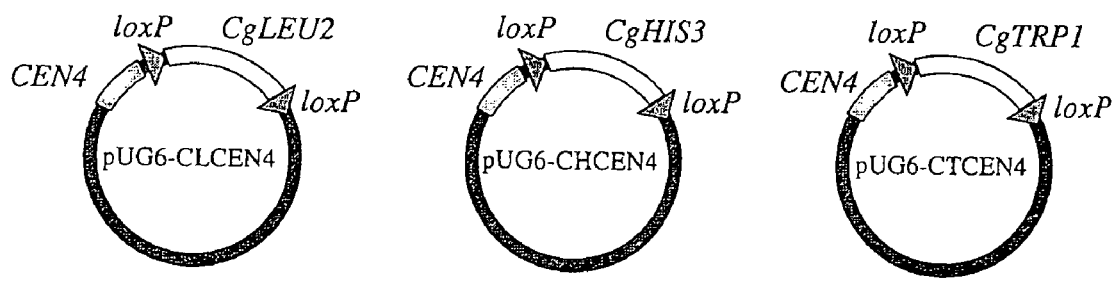
FIG. 13 is a schematic view of plasmids pUG6-CLCEN4, pUG6-CHCEN4 and pUG6-CTCEN4 that are used as templates for preparation of chromosome splitting vectors.

A DNA fragment of about 0.85 kbp containing CEN4 obtained by digesting the plasmid pT7-CEN4(S/X) with XhoI/SalI was recovered from an agarose gel with GENE CLEAN II KIT (Funakoshi Co. Ltd.). Then, a plasmid pUG6-CgHIS3, a plasmid pUG6-CgLEU2, and a plasmid pUG6-CgTRP1 containing marker genes shown in FIG. 12 were digested with SalI, and DNA fragments were recovered from the agarose gel with GENE CLEAN II KIT (Funakoshi Co. Ltd.). Then, the DNA fragment of about 0.85 kbp containing CEN4 was inserted in the SalI site of each of the recovered fragments of plasmids pUG6-CgLEU2, pUG6-CgHIS3 and pUG6-CgTRP1 so that plasmids pUG6-CLCEN4, pUG6-CHCEN4 and pUG6-CTCEN4 were constructed (FIG. 13). In these plasmids, loxP, which is the target sequence of a Cre recombinase, is inserted, and CgLEU2, CgHIS3 and CgTRP1 genes, which are selection markers, can be removed by expressing the Cre recombinase.

C. Sequential Splitting of Chromosome I of Transformant 8

Figure 14B:
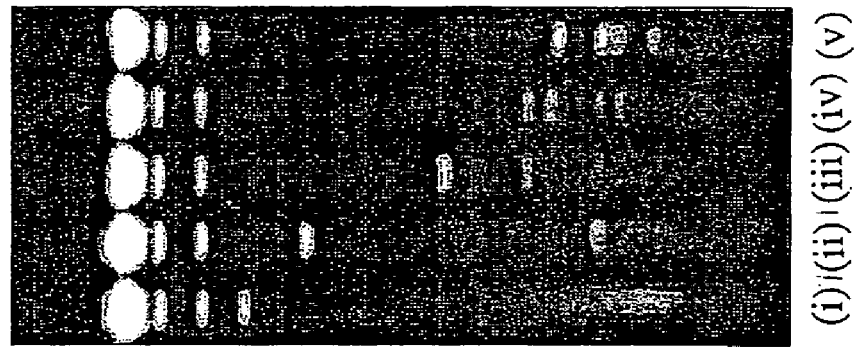
FIG. 14B is a photograph of PFGE showing the process of the sequential splitting.
Figure 14A:
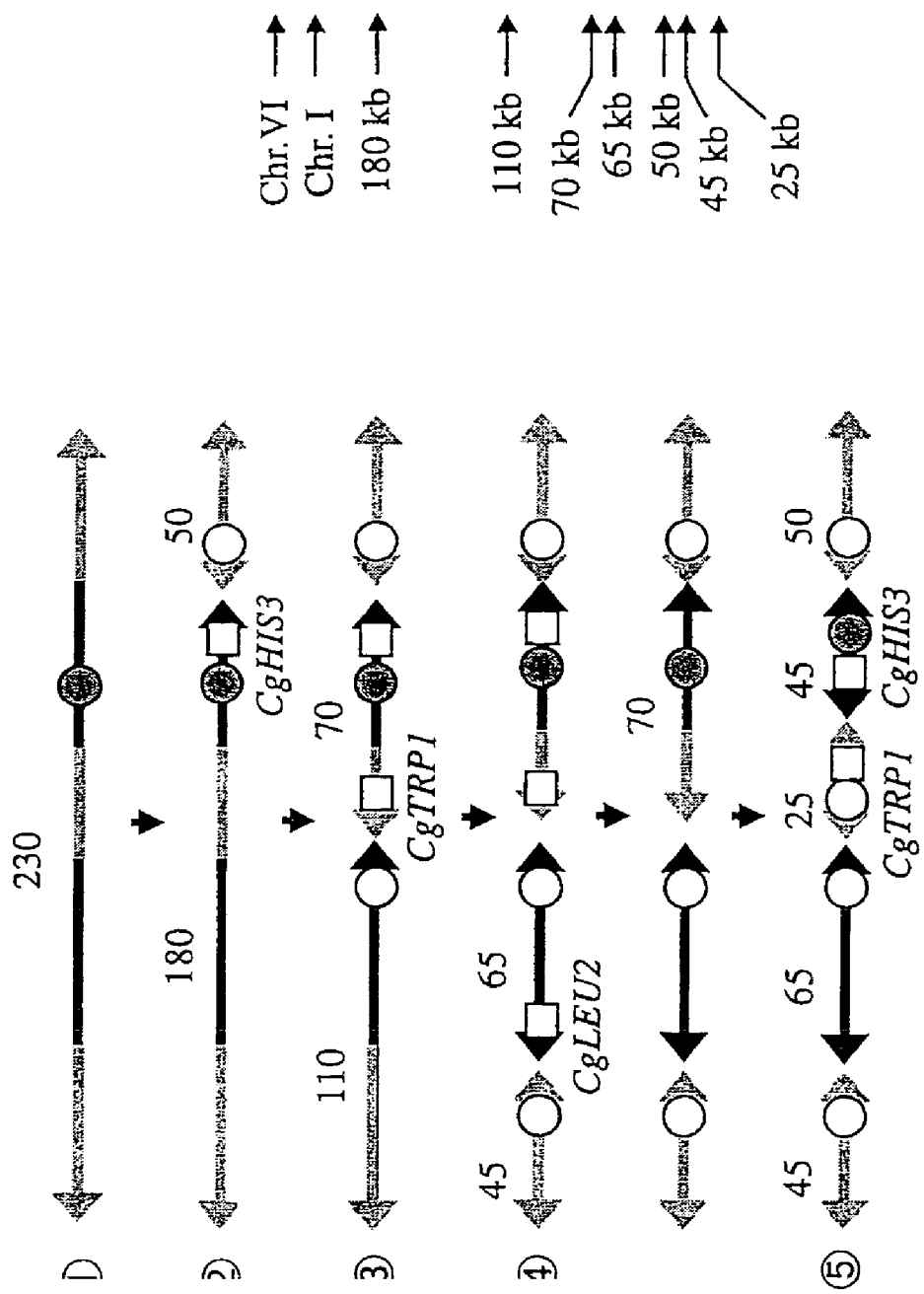
FIG. 14A is a schematic view in which the first chromosome of yeast is sequentially split.
Figures 15A, 15B, 15C, 15D:
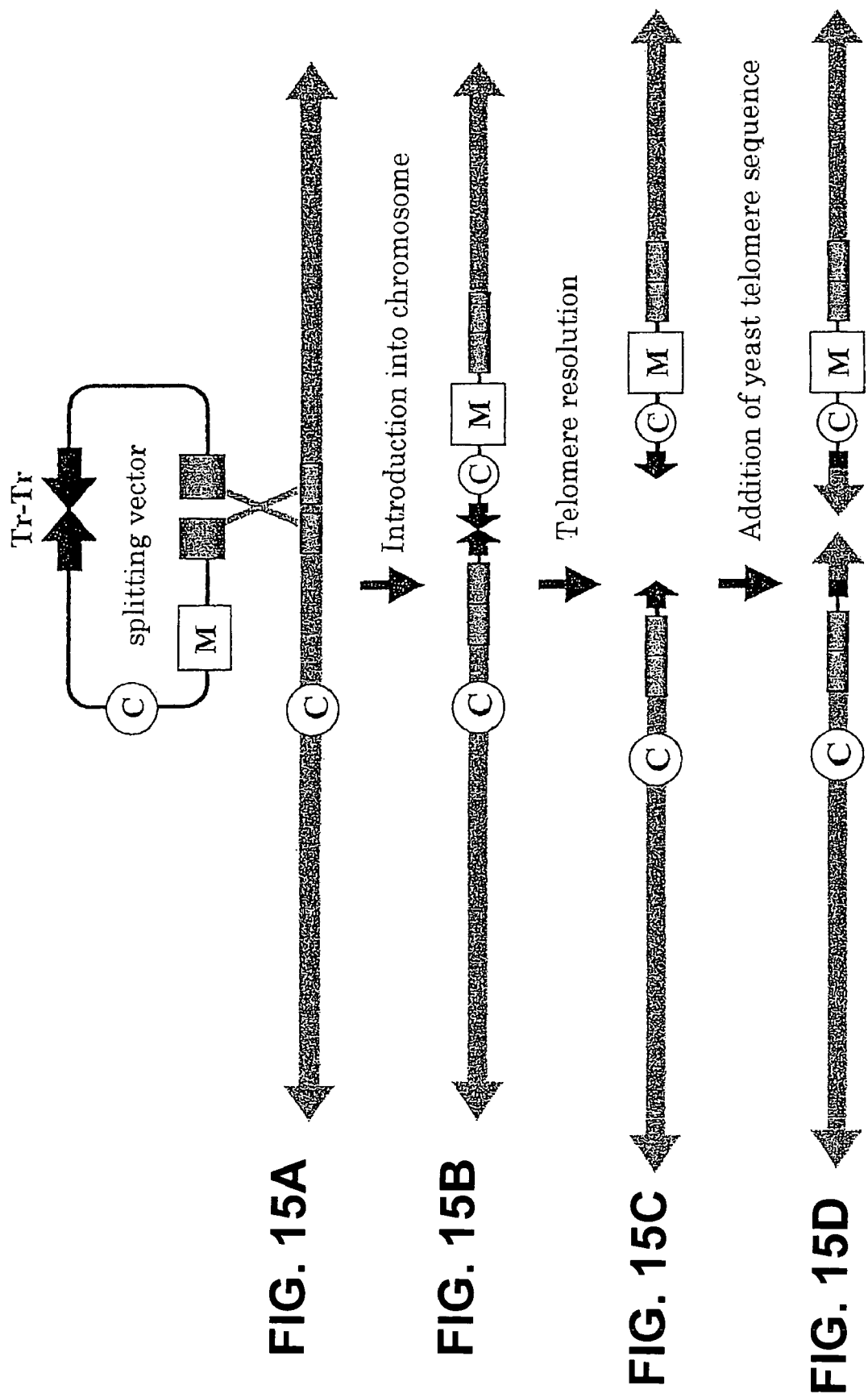
FIGS. 15A to 15D are schematic diagrams showing the basic principle of chromosome splitting.
Figure 16A:
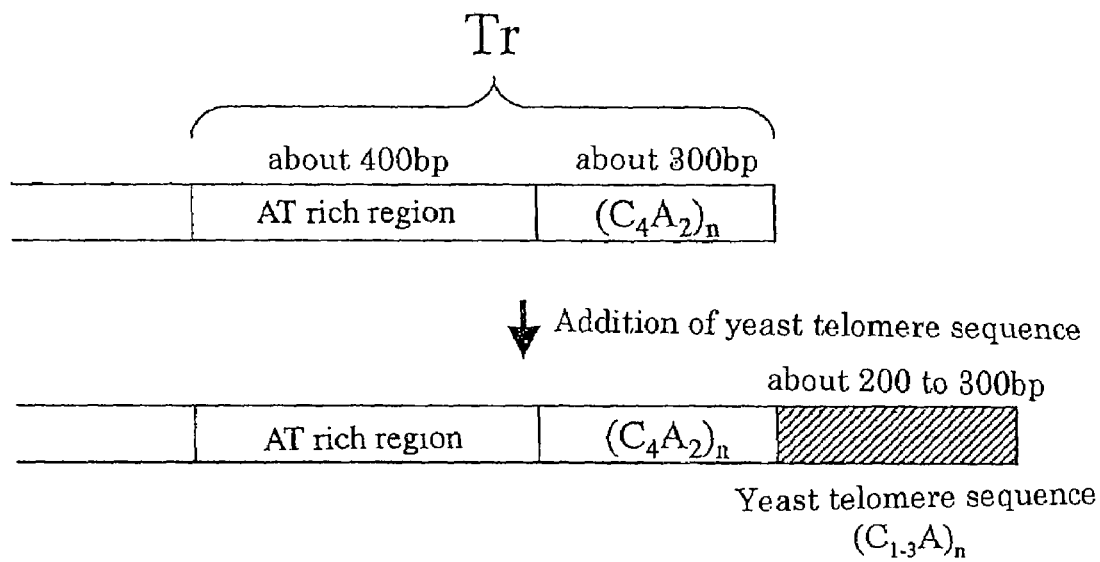
FIGS. 16A and 16B are schematic diagrams showing a telomere sequence of Tetrahymena and addition of a yeast telomere sequence to the telomere sequence of Tetrahymena.
Figure 16B:
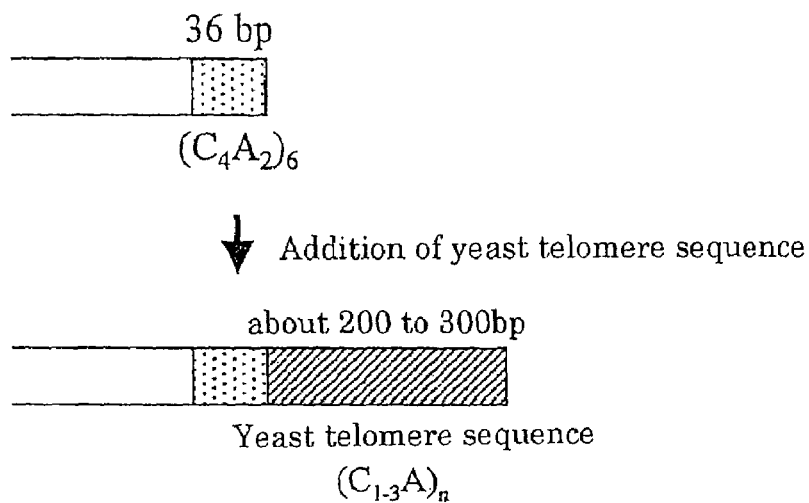

Chromosome I of the transformant 8 having a size of 230 kbp as shown in FIG. 14A (i) is split into two split chromosomes of about 180 kbp and about 50 kbp, as shown in FIG. 14A (ii) and a lane (ii) of FIG. 14B. In this experiment, as shown in FIG. 14A (iii), (iv) and (v), the 180 kbp split chromosome of FIG. 14A (ii) was subsequently split into two chromosomes of about 110 kbp and about 70 kbp (FIG. 14A (iii)) and then the split 110 kbp fragment was further split into two chromosomes of about 45 kbp and about 65 kbp (FIG. 14A (iv)). Then, it was attempted to further split the split-chromosome of about 70 kbp contained in the transformant of FIG. 14A (iv) into two chromosomes of about 25 kbp and about 45 kbp, as designed.

In FIG. 14A, the bold portion is a portion that is believed to contain essential genes for growth so that splitting was planned not to split this portion.

C-1. Splitting of 180 kbp Chromosome

Using primers chI-27 (Sequence ID No.14) and Tr6-4 (Sequence ID No. 20), PCR was performed using the plasmid pUG6-CEN4 as a template so as to prepare the chromosome splitting vector (2D). Furthermore, using primers chI-28 (Sequence ID No. 15) and Tr6-4 (Sequence ID No.20), PCR was performed using the plasmid pUG6-CgTRP1 as a template so as to prepare the chromosome splitting vector (1D). The transformant 8 was transformed with 10 μg of each of the chromosome splitting vectors (ID) and (2D). As a result, 6 of 17 transformants were found that split chromosome of about 180 kbp was subsequently split into about 110 kbp and about 70 kbp, as designed (see the lane (iii) of a PFGE photograph of FIG. 14B). Transformant of this lane (iii) was named as a transformant 8-1 and used in the following experiments.

C-2. Splitting of 110 kbp Chromosome

Using primers chI-29 (Sequence ID No.16) and Tr6-4 (Sequence ID No. 20), PCR was performed using the plasmid pUG6-CEN4 as a template so as to prepare the chromosome splitting vector (2E). Furthermore, using primers chI-30 (Sequence ID No.17) and Tr6-4 (Sequence ID No.20), PCR was performed using the plasmid pUG6-CgLEU2 as a template so as to prepare the chromosome splitting vector (1E). The transformant 8-1 was transformed with 10 μg of each of the chromosome splitting vectors. As a result, 5 of 29 transformants were found that the chromosome of about 110 kbp was split into two chromosomes of about 45 kbp and about 65 kbp, as designed (the lane (iv) of FIG. 14B). Transformants of the lane (iv) of FIG. 14B was named as a transformant 8-2 and used in the following experiments C-3. Splitting of 70 kbp Chromosome First, the selection marker contained in the transformant 8-2 was removed using the Cre-loxP system. A plasmid pSH47, which has a URA3 gene as a selection marker and expresses a Cre recombinase in a galactose-containing medium, was introduced into the transformant 8-2, and was cultured in a YPGa1A medium for 12 hours. Then, the culture was diluted as appropriate so that about 100 colonies appear per plate and was applied onto a YPDA medium. Then, the clones that cannot grow in -Leu, -His, -Trp and -Ura medium were taken as selection marker-removed clones and were used for subsequent chromosome splitting.

Using primers chI-31 (Sequence ID No.18) and Tr6-4 (Sequence ID No. 20), PCR was performed using the plasmid pUG6-CTCEN4 as a template so as to prepare the chromosome splitting vector (2F). Furthermore, using primers chI-32 (Sequence ID No.19) and Tr6-4 (Sequence ID No.20), PCR was performed with the plasmid pUG6-CgHIS3 as a template so as to prepare the chromosome splitting vector (1F). The transformant 8-2 in which the selection markers were removed was transformed with 10 μg of each of the chromosome splitting vectors (1F) and (2F). As a result, 5 of 29 transformants were found that the 70kbp chromosome was split into two chromosomes of about 25 kbp and about 45 kbp, as designed (the lane (v) of FIG. 14B). A Southern blotting analysis was performed with a probe specific to each split chromosome, and it was confirmed that splitting occurred as designed.

As shown in FIGS. 14A and 14B, using the method of the present invention, yeast chromosome I (230 kbp) could be split sequentially into five chromosomes (45, 65, 25, 45, and 50 kbp). A transformant in which a left arm 45 kbp and a right arm 50 kbp of chromosome I are lost can be obtained (data not shown). This may be because that they do not contain essential genes. The operation of the method for splitting a chromosome of the present invention is very simple and allows a desired chromosomal region to be split or removed, so that the method of the present invention is very useful as a method for modifying chromosomes in a large scale.

Figure 17:
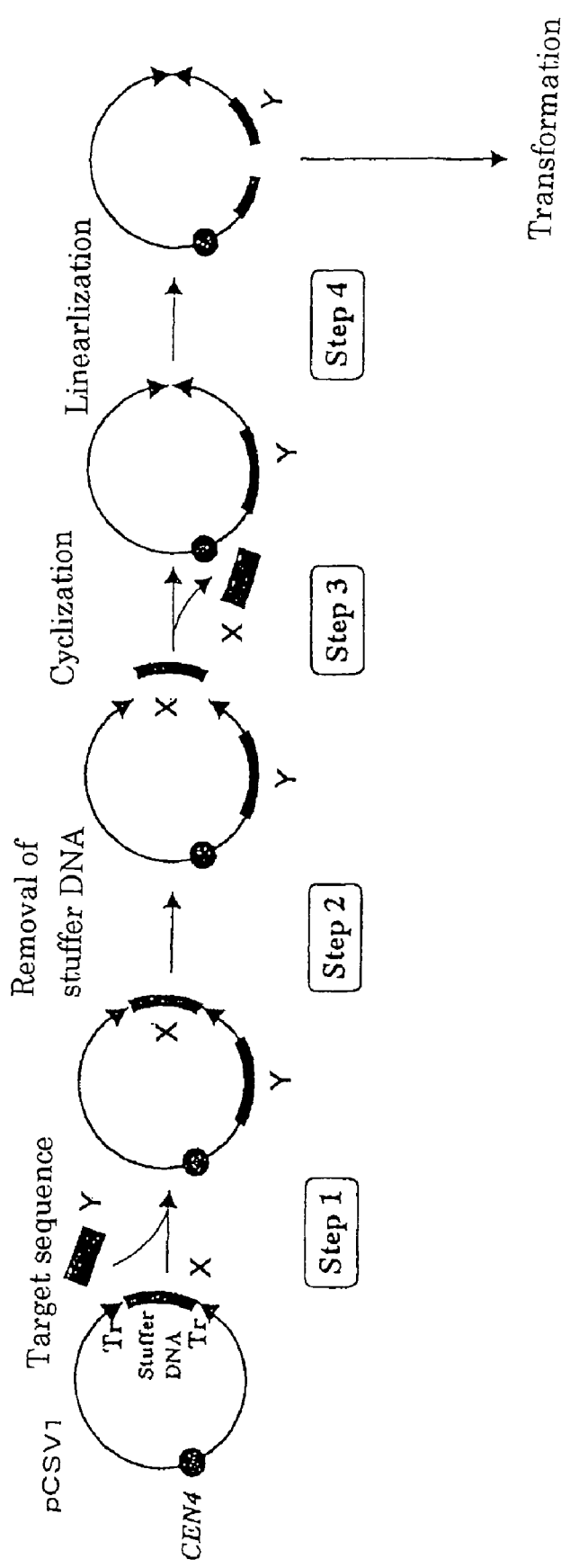
FIG. 17 is a schematic diagram showing a conventional method for splitting a chromosome using pCSV1.
Figure 18A:
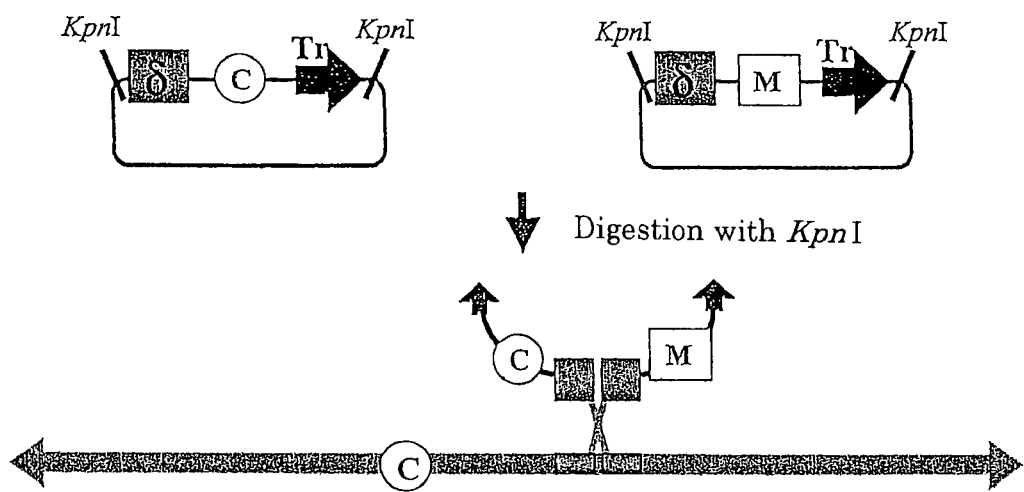
FIGS. 18A and 18B are conventional methods for splitting a chromosome using two splitting vectors having a Tr sequence.
Figure 18B:
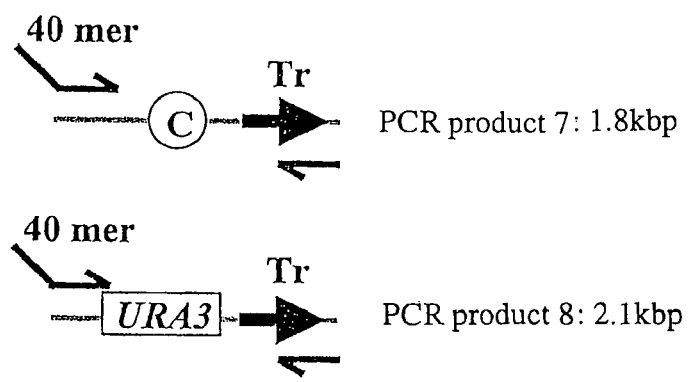
Figure 18C:
FIG. 18C is a photograph of a gel electrophoresis of PCR products when PCR is performed using two splitting vectors as templates.

As described, inventors found that a DNA fragment having a repetitive sequence $(C_4A_2)_n$ (Tr sequence) that conventionally could not be amplified specifically with PCR can be amplified specifically with PCR by setting n of $(C_4A_2)n$ to 6 to 10. It was also found that the chromosome splitting vector can be amplified with PCR in a simple manner by using this $(C_4A_2)_n$ sequence as a primer. Therefore, the present invention can simplify preparation of the chromosome splitting vector remarkably, compared with the conventional method that requires complicated multiple steps for preparation of the chromosome splitting vector as shown in FIG. 17, or the method for preparing two chromosome splitting vectors having a Tr sequence without PCR. In addition, it seems that the chromosome can be split by introducing chromosome splitting vectors having $(C_4A_2)_n$ (n=6 to 10) sequence that is amplified with PCR into a yeast, and a telomere sequence of a yeast is bound to the $(C_4A_2)_n$ sequence that is incorporated into the split chromosome, so that the split chromosome can function as an intact chromosome.

A method of the present invention can be exploited for, for example, splitting or separation of a plant chromosome or an animal chromosome that is cloned into yeast artificial chromosome (YAC) vector. The method of the present invention is also useful for creation of useful transgenic microorganisms, animals or plants, for acceleration of structure analysis of a chromosome and construction of a plant artificial chromosome, speed-up of positional cloning, precision for precise and simplified functional test of microorganism or animal or plant chromosomes and for studies of human chromosome and applications in medicine.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for causing splitting, loss or deletion of a chromosome in a yeast comprising:

preparing a linear chromosome splitting vector (1) in an order consisting essentially of a target sequence (a), a marker gene sequence and $(C_4A_2)_n$ sequence (x);

preparing a linear chromosome splitting vector (2) in an order consisting essentially of a target sequence (b), a centromere sequence of a yeast chromosome and $(C_4A_2)_n$ sequence (y);

simultaneously introducing the chromosome splitting vectors (1) and (2) into a yeast; and selecting yeast on the basis of marker gene expression, wherein the chromosome splitting vectors (1) and (2) are obtained directly by a PCR reaction, wherein at least one primer used in each PCR reaction includes the $(C_4A_2)_n$ sequence, and wherein n is each independently an integer of 6 to 10.

2. The method according to claim 1, wherein n of both $(C_4A_2)_n$ sequences (x) and (y) is 6.

* * * * *